(12) United States Patent
Suzuki et al.

(10) Patent No.: US 7,150,752 B2
(45) Date of Patent: Dec. 19, 2006

(54) ENDOSCOPIC INSTRUMENT

(75) Inventors: Takayuki Suzuki, Yokohama (JP); Masumi Matsushita, Nishitokyo (JP)

(73) Assignee: Olympus Corporation, Tokyo (JP)

( * ) Notice: Subject to any disclaimer, the term of this patent is extended or adjusted under 35 U.S.C. 154(b) by 612 days.

(21) Appl. No.: 10/190,643

(22) Filed: Jul. 8, 2002

(65) Prior Publication Data

US 2004/0006256 A1    Jan. 8, 2004

(51) Int. Cl.
*A61B 17/10*    (2006.01)
*A61B 1/00*    (2006.01)

(52) U.S. Cl. .................. 606/141; 600/132; 600/147; 600/149

(58) Field of Classification Search ............. 606/141; 600/132, 147, 149
See application file for complete search history.

(56) References Cited

U.S. PATENT DOCUMENTS

| | | | |
|---|---|---|---|
| 5,301,656 A * | 4/1994 | Negoro et al. ............. 600/149 |
| 5,462,559 A * | 10/1995 | Ahmed .................... 606/140 |
| 5,735,861 A | 4/1998 | Peifer et al. ............... 606/141 |
| 6,007,551 A * | 12/1999 | Peifer et al. ............... 606/140 |
| 6,315,782 B1 * | 11/2001 | Chu et al. .................. 606/113 |
| 6,679,835 B1 * | 1/2004 | Moriyama ................ 600/133 |
| 2001/0025135 A1 * | 9/2001 | Naito et al. ............... 600/156 |

* cited by examiner

*Primary Examiner*—Michael J. Hayes
*Assistant Examiner*—Victor X. Nguyen
(74) *Attorney, Agent, or Firm*—Scully, Scott, Murphy & Presser

(57) ABSTRACT

A fitting hole portion of a shaft portion fitted to a mouth ring portion of an endoscope is provided to an attachment portion of a ligation band operation band, and an operation to switch between a flange portion insertion position at which the flange portion of the mouth ring is insertable and an engagement position at which a protrusion portion of the mouth ring portion is engagable is performed by a sliding member slidable with respect to the shaft portion.

23 Claims, 13 Drawing Sheets

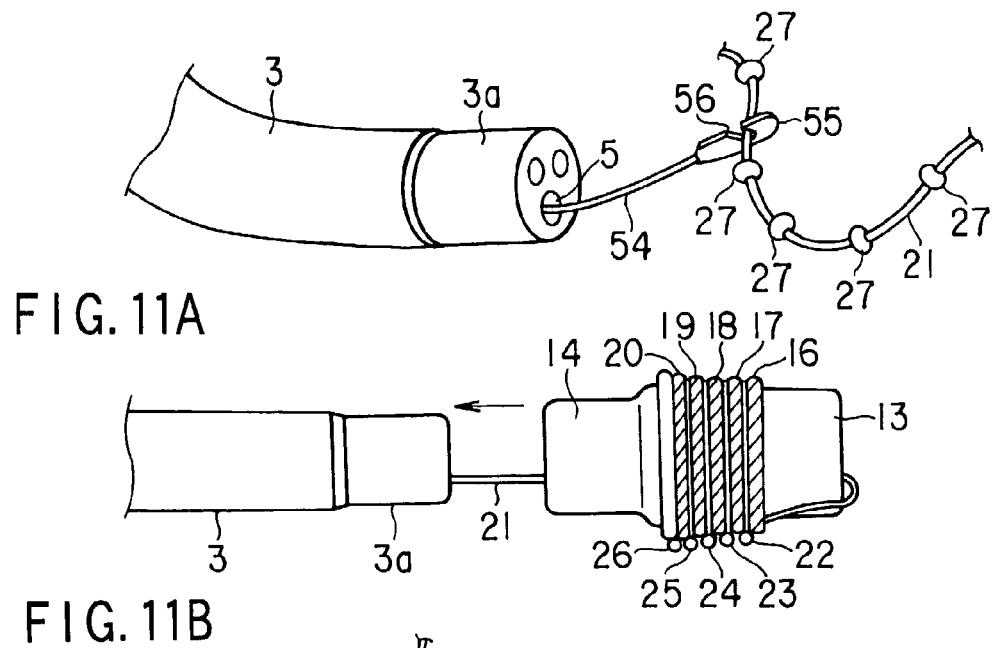
FIG. 11A
FIG. 11B
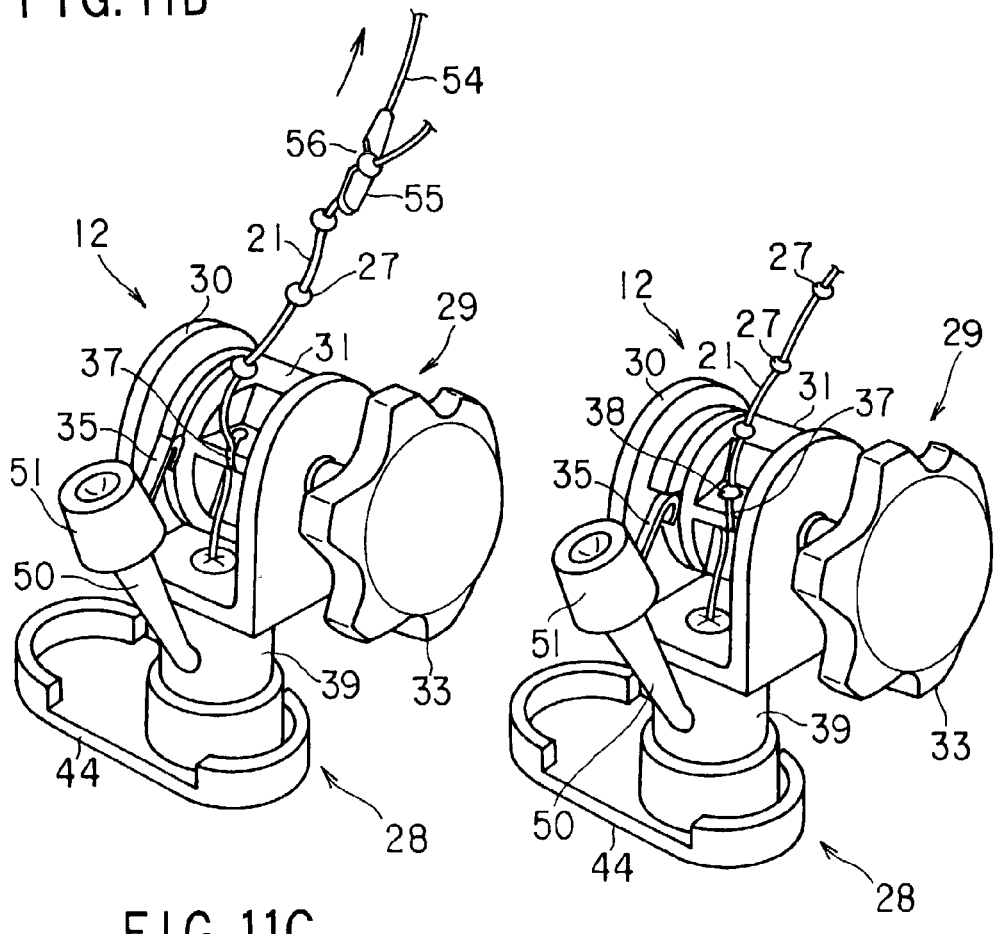
FIG. 11C
FIG. 11D

ENDOSCOPIC INSTRUMENT

BACKGROUND OF THE INVENTION

1. Field of the Invention

The present invention relates to an endoscopic instrument which continuously ligates living tissues in a medical treatment for a gastric or esophageal varix or excision for a polyp or mucosa.

2. Description of the Related Art

Generally, as an apparatus enabling continuous ligation of living tissues, for example, a ligator a having a structure shown in FIG. 17 (Saeed Multi-Band Ligators Sixshooter Wilson-Cook Medical Inc.) is commercially available.

A tubular member b which can be attached to an end of an insertion portion of an endoscope h is provided to this ligator a, as shown in FIGS. 18A and 18B. A plurality of, which is six in this example, ring elastic ligation bands c1 to c6 are sequentially expanded and wound around the outer peripheral surface of the tubular member b.

Further, two operation cords f and g which can be inserted into a channel h1 in the endoscope h are provided to the ligator a. Six operation beads d1 to d6 whose number is equal to that of the elastic ligation bands c1 to c6 are fixed at an end portion of one operation cord f. Similarly, six operation beads e1 to e6 are fixed at an end portion of the other operation cord g. Furthermore, the respective operation beads d1 to d6 and e1 to e6 are engaged with the respective ligation bands c1 to c6. As a result, the respective operation beads d1 to d6 and e1 to e6 are set on the outer peripheral surface of the tubular member b together with the ligation bands c1 to c6. Moreover, the operation cords f and g are inserted into the channel h1 of the endoscope h and extended to the operation portion of the endoscope h.

In addition, when using the ligator a, an operator causes living tissues to be sucked into the tubular member b through the channel h1 of the endoscope h. Thereafter, the ring elastic ligation bands c1 to c6 are sequentially drawn from the end portion side of the tubular member b toward the end portion by pulling the operation cords f and g toward the front side. As a result, the ligation bands c1 to c6 can be removed from the tubular member b in order. At this moment, with the respective ligation bands c1 to c6 being wound around the living tissues sucked to the tubular member b, the living tissues at a plurality of positions can be ligated.

Additionally, for example, U.S. Pat. No. 5,735,861 discloses an operation instrument i which facilitates the operation for pulling the two operation cords f and g of the ligator a toward the front side (see FIGS. 19A to 19C). To the operation instrument i illustrated in this example is provided a substantially U-shaped bearing holder j as shown in FIG. 19A. A take-up shaft m which takes up the operation cords f and g is rotatably supported by the holder j. A handle n is connected to one end portion of the take-up shaft m. Further, a base end portion of a tubular insertion shaft t is connected to the holder j through a tapered shaft portion t1.

Furthermore, when using the operation instrument i, as shown in FIG. 19B, the two operation cords f and g are drawn to the take-up shaft m side of the holder j through the channel h1 of the endoscope h and the lumen of the insertion shaft t of the operation instrument i and fixed to the take-up shaft m. In this state, the insertion shaft t is inserted into a mouth ring portion h3 of the channel h1 opened to the operation portion h2 of the endoscope h as shown in FIG. 19C. Moreover, the operation cords f and g are wound around the take-up shaft m by rotating the handle n of the operation instrument i. As a result, the ligation bands c1 to c6 are removed from the tubular member b in order, thereby ligating the living tissues.

In addition, an airtight valve s such as a forceps tap is attached to the mouth ring portion h3 of the channel h1 of the endoscope h as shown in FIG. 19B. Additionally, as shown in FIG. 19C, when the insertion shaft t of the operation instrument i is inserted into the mouth ring portion h3 of the channel h1 of the endoscope h through the airtight valve s, the operation instrument i can be detachably engaged with the mouth ring portion h3 of the channel h1 in the endoscope h.

Meanwhile, the airtight valve s such as a forceps tap attached to the mouth ring portion h3 of the channel h1 in the endoscope h is generally constituted by an elastic member such as rubber. Therefore, when the insertion shaft t of the operation instrument i disclosed in U.S. Pat. No. 5,735,861 is inserted into and fixed to the mouth ring portion h3 of the channel h1 in the endoscope h through the airtight valve s, a problem such as unstableness occurs even after the operation instrument i is attached to the mouth ring portion h3 of the channel h1 in the endoscope h, and the operation instrument i can not be stabilized.

Further, the tapered shaft t1 of the insertion shaft t and a tapered hole u on the inner surface of the channel h1 on the opening end portion side are fixed to each other by frictional engagement as shown in FIG. 19C. Therefore, fixation of the operation instrument i becomes loose when the strong force is applied to the insertion shaft t of the operation instrument i in order to ligate the living tissues, and the operational feeling when rotating the handle n of the operation instrument i may be possibly deteriorated.

On the other hand, when applying the tension to the operation cord f in order to remove the ligation bands c1 to c5, the handle n must be always held in order to prevent the handle n from rotating in the reverse direction due to reaction force, which degrades the operational feeling. As a method for solving this problem, there is an operation instrument (Speedband Multiple Band Ligator Boston Scientific Corp.) shown in FIGS. 20 to 23 as a commercially available prior art product.

This is a product obtained by providing a one-way clutch which prevents the take-up shaft m from rotating in the reverse direction to the main body of the operation instrument as shown in FIG. 21. The one-way clutch prevents the take-up shaft m from rotating in the reverse direction when an engagement claw p of a spring o fixed to the main body of the operation instrument is engaged with recess portions q1 and q2 provided on the outer periphery of the take-up shaft m at a fixed interval r. Here, the recess portions q1 and q2 have a length corresponding to an interval r' required for each of the elastic ligation rings c1 to c5 to be removed from the tubular member. Therefore, the ligation bands c1 to c5 are removed from the end every time the claw p engages with the recess portions q1 and q2. That is, one of the ligation bands c1 to c5 is removed per click caused due to engagement of the claw p with the recess portion q.

The operation instrument having the structure shown in FIGS. 20 to 23 has the following problem.

The ligation bands are removed one by one every time one click occurs which is generated due to engagement of the claw p with the recess portions q1 and q2 at fixed intervals r. On the other hand, since the entire length of the channel of the non-illustrated endoscope differs depending on models, the phase between the interval r on the front side and interval r' at which the ligation bands are removed varies in accordance with each model of the endoscope. When the phase difference becomes maximum, there occurs a problem that the ligation bands c1 to c6 stop during movement on the tubular member b.

Thus, in the operation instrument having the structure shown in FIGS. 20 to 23, the operation portion i is attached to the endoscope, the recess portions q1 and q2 are then set to initial positions, and the operation cord f is thereafter fixed to a slit w of the take-up shaft m without slacks. As a result, the phase of the interval r on the front side and the interval r' on the end side can be uniquely determined irrespective of the entire length of the channel of the endoscope.

However, engagement of the operation cord f with the slit w must withstand the capacity for operating the ligation bands c1 to c5. Therefore, in the structure shown in FIGS. 20 to 23, the operation cord f is led out from a lead-out hole x (shown in FIG. 20) of the take-up shaft m through a side hole y (shown in FIG. 23) of the take-up shaft m and fixed to the slit w provided to the side surface y, which complicates the structure and the operation.

BRIEF SUMMARY OF THE INVENTION

In view of the above-described problem, it is an object of the present invention to provide an endoscopic instrument which can be easily and assuredly attached to an endoscope.

To achieve this aim, according to the present invention defined in claim 1, there is provided an endoscopic instrument, an operation portion of an endoscope having a mouth ring portion of a channel into which a main body of the endoscopic instrument used in combination with the endoscope is inserted, the mouth ring portion having a protrusion portion which protrudes from the operation portion to the outer side and a flange portion arranged at an edge portion of the protrusion portion, the endoscopic instrument main body having an attachment portion attached to the mouth ring portion, wherein the attachment portion has a mouth ring fitting portion fitted to the mouth ring portion, the mouth ring fitting portion having:

a cylindrical shaft portion including at a shaft center portion a fitting hole portion fitted to the mouth ring portion; and an engagement operation portion which is supported on the shaft portion and operates to switch between a flange portion insertion position at which the flange portion of the mouth ring portion can be inserted and an engagement operation position at which it can be engaged with the protrusion portion of the mouth ring portion.

Further, in the present invention defined in claim 1, in case of performing the operation for attaching the endoscopic instrument main body to the endoscope, the engagement operation portion is set at the flange portion insertion position when fitting the fitting hole portion of the mouth ring fitting portion to the mouth ring portion. In this state, the flange portion of the mouth ring portion is inserted into the mouth ring fitting portion. Then, the engagement operation portion of the endoscopic instrument main body is operated to switch to the engagement position at which it is engaged with the protrusion portion of the mouth ring portion, thereby fixing the endoscopic instrument main body to the mouth ring portion of the endoscope.

Thus, according to the present invention defined in claim 1, the endoscopic instrument main body can be assuredly fixed to the mouth ring portion with a simple operation by operating the engagement operation portion of the endoscopic instrument main body to switch to the engagement position and engaging the engagement operation portion with the protrusion portion of the mouth ring. Therefore, since attachment to the endoscope is easy and assembling/disassembling can be rapidly performed, the advantage of reduction in treatment time can be expected.

Furthermore, according to the present invention defined in claim 2, there is provided the endoscopic instrument according to claim 1, wherein the engagement operation portion has a sliding member which can move along the protrusion portion and the sliding member has a guide hole into which the protrusion portion of the mouth ring portion is slidably inserted; and wherein the guide hole has a large-diameter hole portion into which the flange portion of the mouth ring portion can be inserted, an engagement hole portion with which the protrusion portion of the mouth ring portion can be engaged, and a communication portion which communicates between the large-diameter hole portion and the engagement hole portion.

Moreover, in the present invention according to claim 2, in case of performing the operation for attaching the endoscopic instrument main body to the endoscope, the sliding member of the engagement operation portion is set at the flange portion insertion position when fitting the fitting hole portion of the mouth ring fitting portion to the mouth ring portion. In this state, with the large-diameter hole portion of the sliding member being positioned to the flange portion of the mouth ring portion, the flange portion of the mouth ring portion is inserted into the mouth ring fitting portion by fitting the attachment portion of the endoscopic instrument main body on the mouth ring portion of the endoscope. Then, the sliding member of the engagement operation portion is slid along the protrusion portion of the mouth ring portion and the engagement hole portion is moved to engage with the protrusion portion of the mouth ring portion from the large-diameter hole portion of the sliding member through the communication portion, thereby fixing the endoscopic instrument main body to the mouth ring portion of the endoscope.

Therefore, the equipment operation portion can be securely fixed to the endoscope with a simple operation by reducing the diameter of the engagement hole portion and fixing it to the mouth ring of the endoscope. Thus, since assembling/disassembling can be rapidly carried out, the advantage of reduction in treatment time can be expected. In addition, since secure fixing can be enabled as compared with frictional engagement, it is possible to perform the treatment with the excellent operation feeling without causing looseness or movement even if the large force is applied to the connection portion during the treatment.

Additionally, according to the present invention defined in claim 3, there is provided the endoscopic instrument according to claim 2, wherein the engagement operation portion has an actuation guide which guides the sliding operation that the sliding member moves along the guide hole between an engagement releasing position at which the protrusion portion is inserted into the large-diameter hole portion and an engagement position at which the protrusion portion is engaged with the engagement hole portion.

Further, in the present invention defined in claim 3, the sliding operation is guided by the actuation guide when performing the sliding operation of the sliding member along the guide hole.

Furthermore, according to the present invention defined in claim 4, there is provided the endoscopic instrument according to claim 3, wherein the actuation guide has a guide groove formed to the sliding member in contiguity with at least one side portion part of the guide hole; and wherein the shaft portion has a sliding guide which is inserted to the guide groove.

Moreover, in the present invention defined in claim 4, the sliding operation is guided by the guide groove of the actuation guide and the sliding guide when performing the sliding operation of the sliding member along the guide hole.

In addition, in the present invention defined in claim 5, there is provided the endoscopic instrument according to claim 1, wherein the endoscopic instrument main body is an endoscopic ligation apparatus which ligates a tissue in a living body.

Additionally, in the present invention defined in claim 5, in case of performing the operation for attaching the ligation band operation portion of the endoscopic ligation apparatus to the mouth ring of the endoscope, with the large-diameter hole portion of the engagement operation portion of the ligation band operation portion being positioned at the flange portion of the mouth ring portion, the ligation band operation portion is fitted on the mouth ring portion of the endoscope. Then, the engagement operation portion of the ligation band operation portion is slid along the protrusion portion of the mouth ring portion and the engagement hole portion is moved to engage with the protrusion portion of the mouth ring from the large-diameter hole portion of the engagement portion through the communication portion, thereby fixing the ligation band operation portion to the mouth ring portion of the endoscope.

Further, according to the present invention defined in claim 6, there is provided the endoscopic instrument according to claim 5, wherein the endoscopic ligation apparatus comprises:

a substantially cylindrical attachment which can be attached at an end part of the insertion portion of the endoscope and has a ligation band which ligates a tissue in a living body being detachably fitted thereon;

an operation cord which is inserted into the channel, the operation cord having an end portion at which the engagement portion detachably engaging with the ligation band is arranged and a base end portion which extends to the operation portion side; and a ligation band operation portion which is attached to the mouth ring portion and gives tensile force toward the front side to the operation cord.

Furthermore, according to the present invention defined in claim 7, there is provided the endoscopic instrument according to claim 6, wherein the attachment has a plurality of the ligation bands;

wherein the operation cord has a plurality of anchor members which respectively engage with the respective ligation bands; and wherein the anchor member is formed into a cylindrical shape coaxial with the operation cord.

Moreover, according to the present invention defined in claim 8, there is provided the endoscopic instrument according to claim 7, wherein the anchor member is set in such a manner that a ratio of its length L2 in the axial direction of the operation cord and its length D1 in the radial direction is larger than 1.

In addition, according to the present invention defined in claim 9, there is provided the endoscopic instrument according to claim 6, wherein the operation cord has a plurality of the anchor members being arranged at fixed intervals;

wherein the interval has a length which is substantially the same as an outer peripheral length of the attachment; and wherein the attachment has an anchor member alignment portion by which the anchor members are aligned in the axial direction of the attachment when the operation cord is spirally wound on the outer periphery of the attachment.

Additionally, according to the present invention defined in claim 10, there is provided an endoscopic instrument used in combination with an endoscope, wherein the endoscopic instrument is an endoscopic ligation apparatus which ligates a tissue in a living body, the endoscopic ligation apparatus comprising:

an attachment which can be attached at an end of the endoscope and has at least one ligation band fitted thereon;

one operation cord which is inserted into a channel of the endoscope from the attachment;

an equipment operation portion which is fixed in the vicinity of the operation portion of the endoscope and gives a pulling operation toward the front side to the operation cord;

a take-up shaft of the operation cord which is supported by the equipment operation portion so as to be capable of swiveling;

a fixing portion of the operation cord provided on the peripheral surface of the take-up shaft; and a plurality of coupling points in a range where the operation cord and the equipment operation portion exist.

Further, in the present invention, by providing a plurality of coupling points in a range where a connection portion of the operation cord and the equipment operation exists, attachment is always enabled without causing slack of the operation cord even if the entire length of the channel fluctuates depending on a type of the endoscope.

Furthermore, according to the present invention defined in claim 11, there is provided the endoscopic instrument according to claim 10, wherein the operation cord has a cord connection portion on the front side; and wherein a plurality of either the fixing portions or the cord connection portions are provided at predetermined intervals.

Moreover, according to the present invention defined in claim 12, there is provided the endoscopic instrument according to claim 11, wherein the endoscopic ligation apparatus has a plurality of the fixing portions and the one cord connection portion.

In addition, according to the present invention defined in claim 13, there is provided the endoscopic instrument according to claim 11, wherein the endoscopic instrument ligation apparatus has the one fixing portion and a plurality of the cord connection portion.

Additionally, according to the present invention defined in claim 14, there is provided an endoscopic instrument used in combination with an endoscope, wherein the endoscopic instrument is an endoscopic ligation apparatus which ligates a tissue in a living body, the endoscopic ligation apparatus comprising:

an attachment which can be attached at an end of the endoscope and has at least one ligation band fitted thereon;

one operation cord which is inserted into a channel of the endoscope from the attachment;

an equipment operation portion which is fixed in the vicinity of the operation portion of the endoscope and gives a pulling operation toward the front side to the operation cord;

a take-up shaft of the operation cord which is supported by the equipment operation portion so as to be capable of swiveling; and a fixing portion of the operation cord which is provided on the peripheral surface of the take-up shaft, the fixing portion including a groove which can hold the operation cord and a protrusion portion that the operation cord can be wound around and fixed to.

Further, according to the present invention defined in claim 15, there is provided an endoscopic instrument used in combination with an endoscope, wherein the endoscopic instrument is an endoscopic ligation apparatus which ligates a tissue in a living body, the endoscopic ligation apparatus comprising:

an attachment which can be attached at an end of the endoscope and has at least one ligation band fitted thereon;

one operation cord which is inserted into a channel of the endoscope from the attachment;

an equipment operation portion which is fixed in the vicinity of the operation portion of the endoscope and gives a pulling operation toward the front side to the operation cord;

a take-up shaft of the operation cord, the take-up shaft having a cavity therein;

at least one engagement cam which restricts a rotational stroke of the take-up shaft; and an engagement claw which engages with the engagement cam and has the elasticity giving an rotational operation and a fixing operation of the take-up shaft.

Furthermore, in the present invention, an operator can recognize that one ligation operation has terminated from the feeling and sound of click when the engagement cam has engaged with the engagement claw without confirming a screen of the endoscope.

BRIEF DESCRIPTION OF THE SEVERAL VIEWS OF THE DRAWING

FIG. 11A is a perspective view of primary parts showing the state in which the operation cord is engaged by a hook of the pulling cord when using the endoscopic ligation apparatus according to the first embodiment;

FIG. 11B is a side view for illustrating the operation for attaching the end attachment to the endoscope;

FIG. 11C is a perspective view showing the state in which the operation cord is engaged in a cord attachment groove on the take-up drum;

FIG. 11D is a perspective view showing the state in which a fixation bead of the operation cord is engaged in a recess of the take-up drum;

DETAILED DESCRIPTION OF THE INVENTION

Figure 1:
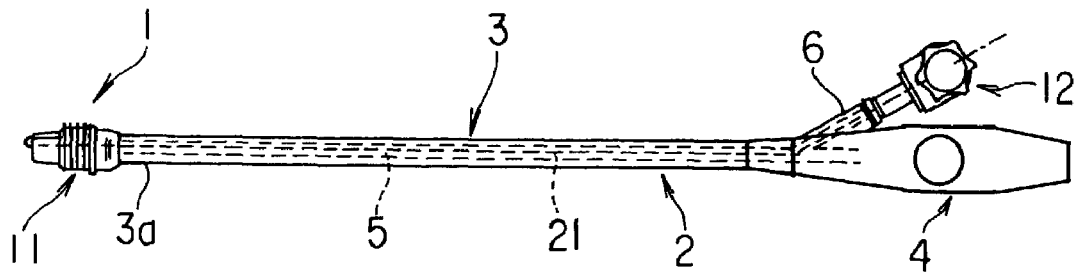
FIG. 1 is a side view showing the state in which an endoscopic ligation apparatus according to a first embodiment of the present invention is assembled in an endoscope.

A first embodiment according to the present invention will now be described with reference to FIGS. 1 to 11D. FIG. 1 shows the state in which an endoscopic ligation apparatus 1 which is an endoscopic instrument according to this embodiment is assembled to an endoscope 2.

Figure 7:
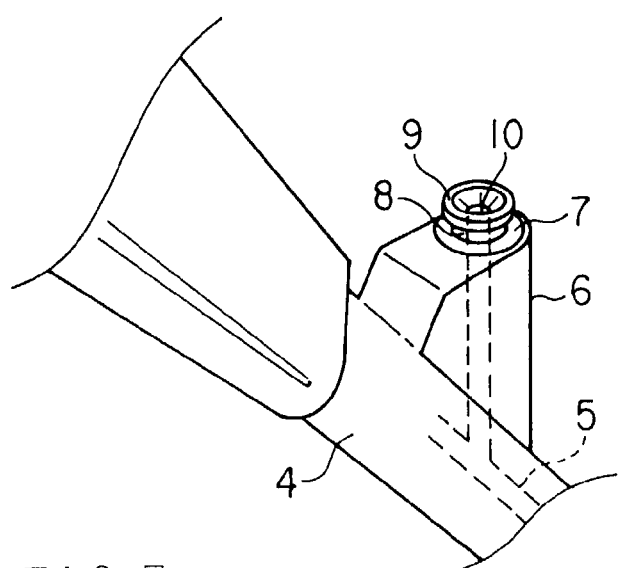
FIG. 7 is a perspective view showing a mouth ring portion of the operation portion in the endoscope to which the endoscope ligator according to the first embodiment is assembled.

Here, an operation portion 4 on the front side is coupled to the endoscope 2 at a base end portion of an elongated insertion portion 3 inserted into a body. Further, as shown in FIG. 7, a mouth ring portion 6 of a forceps channel 5 is formed to the operation portion 4 on the front side. To the mouth ring portion 6 are provided a seat 7, a small-diameter protrusion portion 8 which protrudes from the seat 7 and has a substantially shaft-like shape, a large-diameter flange portion 9 arranged at an edge portion of the protrusion portion 8, and a through hole 10 in the axial direction which pierces a shaft center portion of the protrusion portion 8. Furthermore, the through hole 10 of the mouth ring 6 is caused to communicate with the forceps channel 5.

Moreover, to the endoscopic ligation apparatus 1 according to this embodiment used in combination with the endoscope 2 are provided an end attachment 11 which can be attached at an end portion 3a of an insertion portion 3 in the endoscope 2, and a ligation band operation unit (endoscopic instrument main body) 12 detachably coupled with the mouth ring portion 6 of the operation portion 4 in the endoscope 2.

Figure 2A:
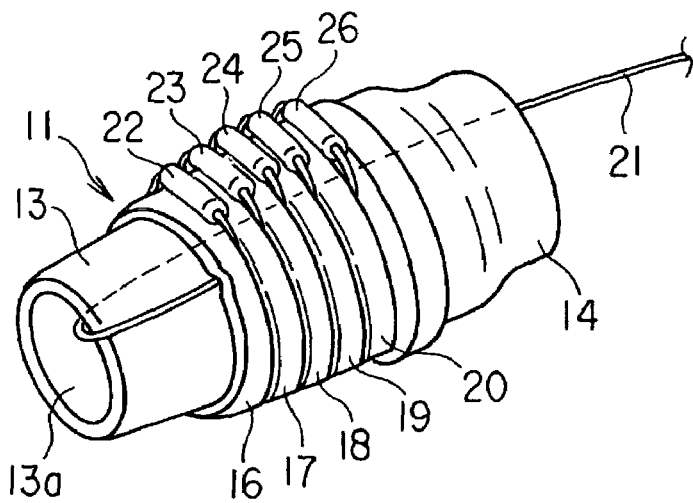
FIG. 2A is a perspective view showing an end attachment in the endoscopic ligation apparatus according to the first embodiment.
Figure 2B:
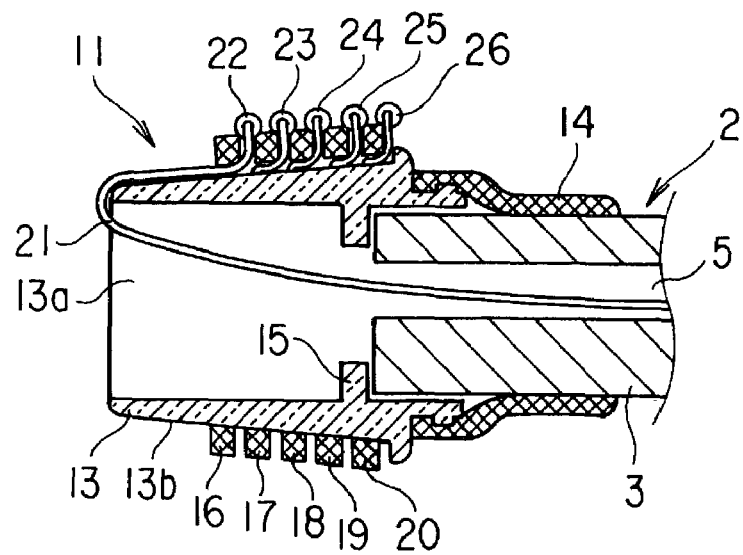
FIG. 2B is a vertical cross-sectional view of primary parts showing the state in which the end attachment of the endoscopic ligation apparatus is assembled in the endoscope.

Here, as shown in FIG. 2B, the end attachment 11 is constituted by a tubular member 13 formed of a material having the transparency so that the inside of a body cavity can be observed in the visual field of the endoscope 2 such as polycarbonate, polystyrene, acrylic, polymethyl pentene, acrylonitrile butadiene/styrene, acrylonitrile styrene or the like, and a hood 14 fixed on the base end portion side of the tubular member 13. In addition, the hood 14 is formed of soft resin such as poly vinyl chloride, polyurethane elastomer, silicon rubber, polystyrene elastomer, polyester elastomer, styrene/ethylene/butadiene/stylene copolymer or the like so that it can be attached to various kinds of endoscopes 2 having different outside diameter dimensions.

Additionally, a substantially annular endoscope impingement portion 15 is provided to a lumen 13a of the tubular member 13 so as to protrude toward the inner side. Further, the end portion 3a of the insertion portion 3 in the endoscope 2 inserted into the lumen 13a of the tubular member 13 impinges to and engages with the endoscope impingement portion 15.

Furthermore, a tapered surface 13b whose outside diameter gradually becomes smaller toward the end side is formed on the outer peripheral surface of the tubular member 13 of the end attachment 11. A plurality of, which is five in this embodiment, ring ligation bands 16 to 20 which ligate living tissues are detachably fitted on the tapered surface 13b. These ligation bands 16 to 20 are made of a very elastic material such as polyurethane, silicon, polystyrene elastomer, or polyisoprene rubber, natural rubber, polyurethane elastomer, silicon rubber, polystyrene elastomer, chloroprene rubber or the like. Moreover, each of the ligation bands 16 to 20 has a ring inside diameter of approximately 1 to 2 mm in the natural state. However, when it is fitted on the end attachment 11, that inside diameter expands to 10 to 15 mm.

Figure 3A:
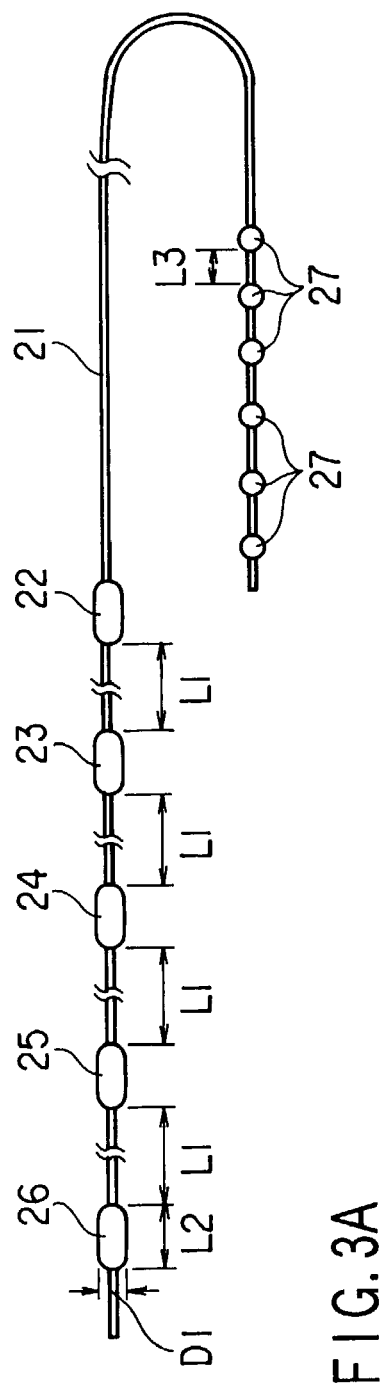
FIG. 3A is a plane view showing an operation cord of the endoscopic ligation apparatus according to the first embodiment.

In addition, an end portion of an operation cord 21 inserted into a forceps channel 5 of the endoscope 2 is detachably engaged with the ligation bands 16 to 20 on the tapered surface 13b of the tubular member 13. As shown in FIG. 3A, operation beads (engagement portions) 22 to 26 whose number is equal to that of the ligation bands 16 to 20 are respectively fixed at the end portion of the operation cord 21 at fixed intervals L1. Additionally, a plurality of fixation beads 27 are fixed to the operation cord 21 at the end portion on the front side.

Here, the operation beads 22 to 26 and the fixation beads 27 have the excellent moldability, are assuredly fixed when molding/fixing resin with the high mechanical strength on the operation cord 21 by injection molding, and can be manufactured with the low cost. Further, when the operation cord 21, the operation beads 22 to 26 and the fixation beads 27 are formed of the same resin and liquid crystal polyester in particular, their adhesiveness is improved, thereby increasing the fixation strength.

Furthermore, in regard to the shape of the operation beads 22 to 26, each of them is formed so as to be symmetrical to the central line of the operation cord 21. Moreover, a length L2 of each of the operation beads 22 to 26 in the axial direction is set necessarily larger than the outside diameter dimension D1. In particular, the optimum aspect ratio is the outside diameter dimension D1: the length L2 in the axial direction=1:2 to 1:3. It is to be noted that the operation beads 22 to 26 may be formed of soft resin such as polyurethane, silicon, polystyrene elastomer or the like.

Figure 3B:
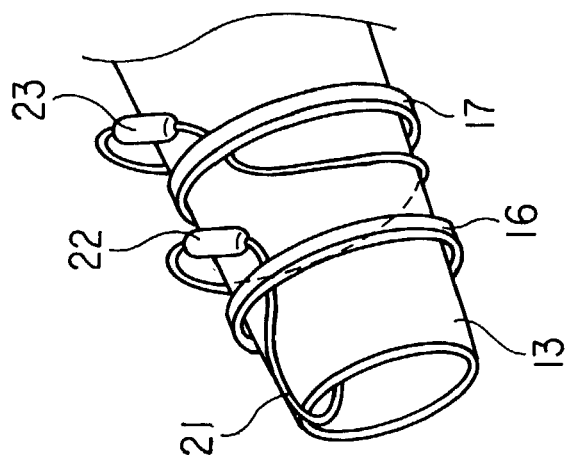
FIG. 3B is a perspective view of primary parts showing the component arrangement state of ligation bands and the operation cord in the end attachment of the endoscopic ligation apparatus.

In addition, the interval L1 between the respective operation beads 22 to 26 at the end portion of the operation cord 21 is set to be substantially equal to the length of the outer peripheral surface of the tubular member 13. Additionally, in the operation for detachably engaging the end portion of the operation cord 21 with the ligation bands 16 to 20 on the tubular member 13, the part between the respective operation beads 22 to 26 at the end portion of the operation cord 21 is cased to pass under the respective ligation bands 16 to 20 and then wound around the outer peripheral surface of the tubular member 13 as shown in FIG. 3B. As a result, the operation cord 21 after assembling is arranged with the part between the respective operation beads 22 to 26 being sandwiched between the tubular member 13 and the respective ligation bands 16 to 20, and one end of each of the operation beads 22 to 26 is brought into contact with and engaged with each of the ligation bands 16 to 20. In this state, as shown in FIG. 2A, the respective operation beads 22 to 26 are aligned in a line in the axial direction.

Further, after the operation cord 21 is engaged with the respective ligation bands 16 to 20 on the outer peripheral surface side of the tubular member 13, it passes through the lumen 13a of the tubular member 13 and is inserted into the lumen of the forceps channel 5 in the endoscope 2 as shown in FIG. 2B. Furthermore, the base end portion side of the operation cord 21 is extended to the outer side from the base end portion side of the forceps channel 5 through a through hole 10 of a mouth ring portion 6 of the operation portion 4 on the front side and coupled with a ligation band operation unit 12.

Figure 4:
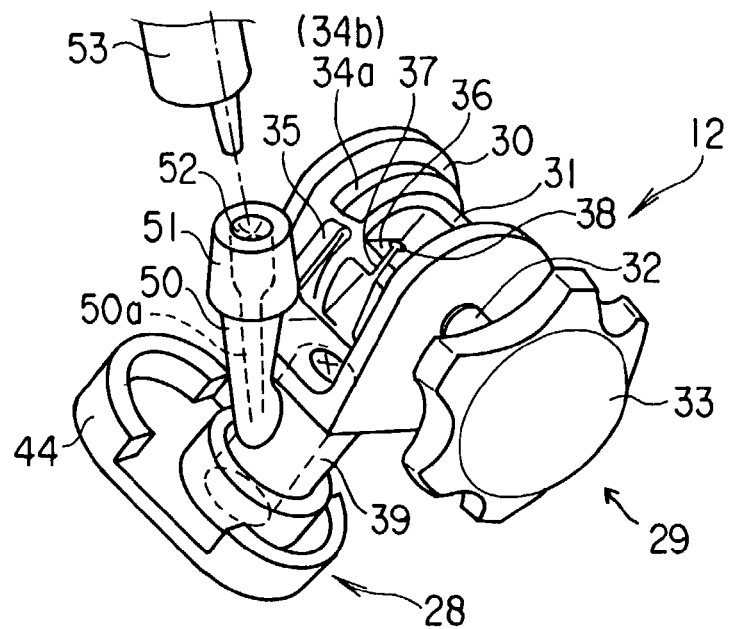
FIG. 4 is a perspective view showing an exterior appearance of an operation portion of the endoscopic ligation apparatus according to the first embodiment.
Figure 5:
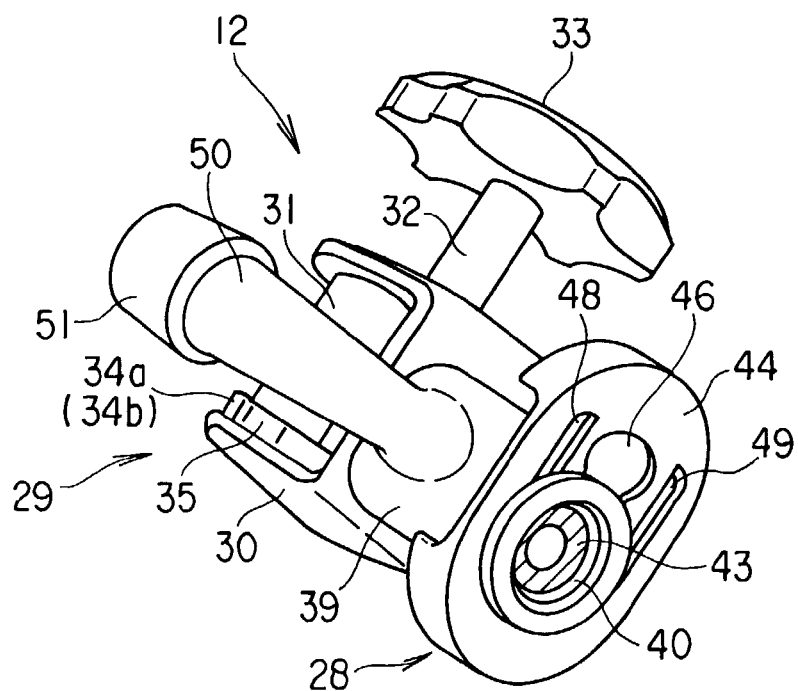
FIG. 5 is a perspective view showing an endoscope coupling portion in the operation portion of the endoscopic ligation apparatus according to the first embodiment.

Moreover, to the ligation band operation unit 12 are provided an attachment portion (mounting portion) 28 to the mouth ring portion 6 of the endoscope 2 and a take-up portion 29 which takes up the operation cord 21, as shown in FIG. 4. Here, a frame member 30 having a substantially U-shaped cross section is provided to the take-up portion 29. A take-up shaft 32 coaxially provided to a shaft center portion of the take-up drum 31 is attached to the frame member 30. One end portion of the take-up shaft 32 is extended to the outer side of the frame member 30 and a handle 33 is attached thereto.

Figure 6A:
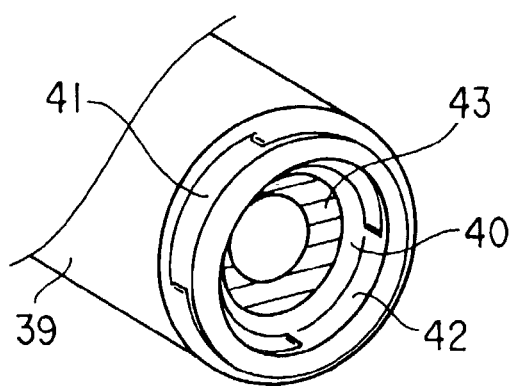
FIG. 6A is a perspective view showing a part of a sliding guide of a housing in the endoscope ligator according to the first embodiment.
Figure 6C:
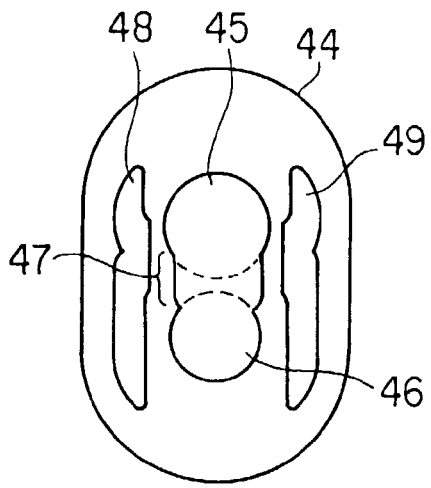
FIG. 6C is a plane view showing the endoscope coupling portion in the operation portion of the endoscopic ligation apparatus.
Figure 6B:
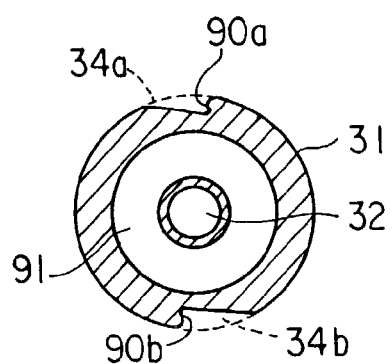
FIG. 6B is a plane view showing an engagement cam on the circumference of a take-up drum.

In addition, two engagement cams 34a and 34b notched in the recess shape along the circumference on the outer peripheral surface are formed to one end portion of the take-up drum 31 at positions distanced away from each other by 180°, as shown in FIG. 6B. Incidentally, although the two engagement cams 34a and 34b exist on the circumference of the take-up drum 31 in this embodiment, the interval L1 between the respective operation beads 22 to 26 at the end portion of the operation cord 21 is set to a length which is a half of the circumferential length of the take-up drum 31 in accordance with these engagement cams.

Additionally, a claw 35 which engages with the engagement cams 34a and 34b of the take-up drum 31 is fixed to the frame member 30. The claw 35 is formed of metal or resin having the resilience and it is pressed against the engagement cams 34a and 34b with a fixed pressure.

Further, steps 90a and 90b are formed to the engagement cams 34a and 34b, respectively. On the other hand, a hollow portion 91 is formed to the inside of the take-up drum 31 so as not to impair the strength as a structure.

Furthermore, as shown in FIG. 4, a cord fixation portion 36 is provided on the circumference of the take-up drum 31. To the cord fixation portion 36 are provided an operation cord attachment groove 37 having one end side being opening and a recess 38 with which the fixation beads 27 of the operation cord 21 can be engaged. Here, the attachment groove 37 of the cord fixation portion 36 is set to be thicker than the diameter of the operation cord 21 and thinner than the fixation beads 27. Moreover, the width of the cord fixation portion 36 is set to be substantially equal to the interval L3 between the respective fixation beads 27.

In addition, in the ligation band operation unit 12, with the operation cord 21 being engaged with and stopped at the cord fixation portion 36, the pulling operation force is given to the front side of the operation cord 21 by rotating the handle 33 to drive the take-up drum 31 to rotate.

Figure 9:
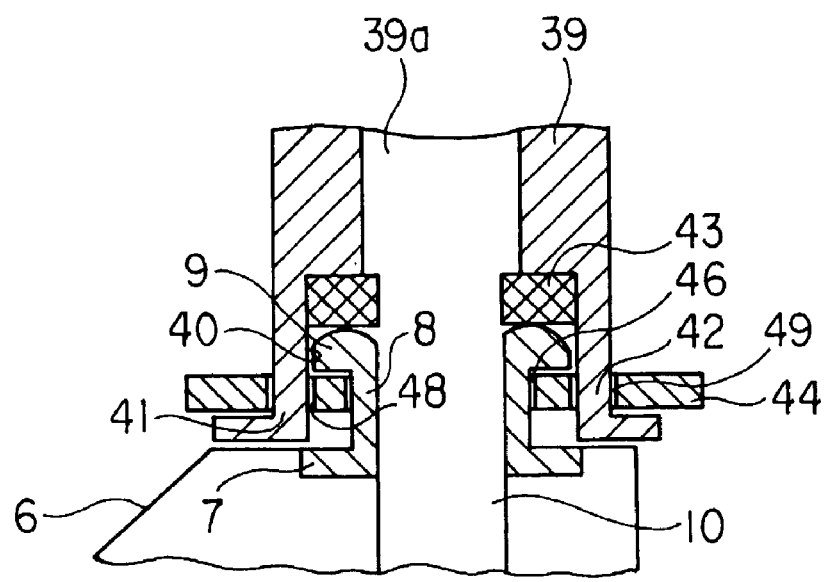
FIG. 9 is a vertical cross-sectional view of primary parts showing a coupling portion between the operation portion of the endoscopic ligation apparatus according to the first embodiment and the operation portion of the endoscope.

Additionally, a substantially cylindrical shaft portion 39 is provided to the attachment portion 28 of the ligation band operation unit 12. As shown in FIG. 9, a fitting hole portion (mouth ring fitting portion) 40 whose diameter is larger than a lumen 39a of the shaft portion 39 is formed to the lower end portion of the shaft portion 39. A flange portion 9 of the protrusion portion 8 at the mouth ring portion 6 in the endoscope 2 is inserted into the fitting hole portion 40.

Further, as shown in FIG. 6A, sliding guides 41 and 42 are formed on the peripheral wall portion of the fitting hole portion 40 of the shaft portion 39. Furthermore, a substantially ring shaped packing 43 is fitted to the inner bottom portion of the fitting hole portion 40. Furthermore, when the attachment portion 28 is attached to the mouth ring portion 6 of the endoscope 2, the flange portion 9 of the mouth ring portion 6 is brought into contact with the packing 43 in the fitting hole portion 40, thereby intercepting a flow of air from the outside to the forceps channel 5 through the fitting hole portion 40 of the shaft portion 39 and the through hole 10 of the mouth ring portion 6.

Moreover, to the shaft portion 39 is attached a substantially tabular sliding member (engagement operation portion) 44 which switches between an engagement position at which the attachment portion 28 of the ligation band operation unit 12 and the mouth ring portion 6 of the endoscope 2 are held in the engagement state when the attachment portion 28 is attached to the mouth ring portion 6 and an engagement releasing position at which engagement between these members is released. As shown in FIG. 6C, to the sliding member 44 are formed a large-diameter hole portion 45 into which the flange portion 9 of the mouth ring portion 6 can be inserted, an engagement hole portion 46 with which the protrusion portion 8 of the mouth ring portion 6 can be engaged, and a communication portion 47 which causes the large-diameter hole portion 45 and the engagement hole portion 46 to communicate with each other. Here, the diameter of the engagement hole portion 46 is set larger than the protrusion portion 8 and smaller than the flange portion 9.

Figure 10A:
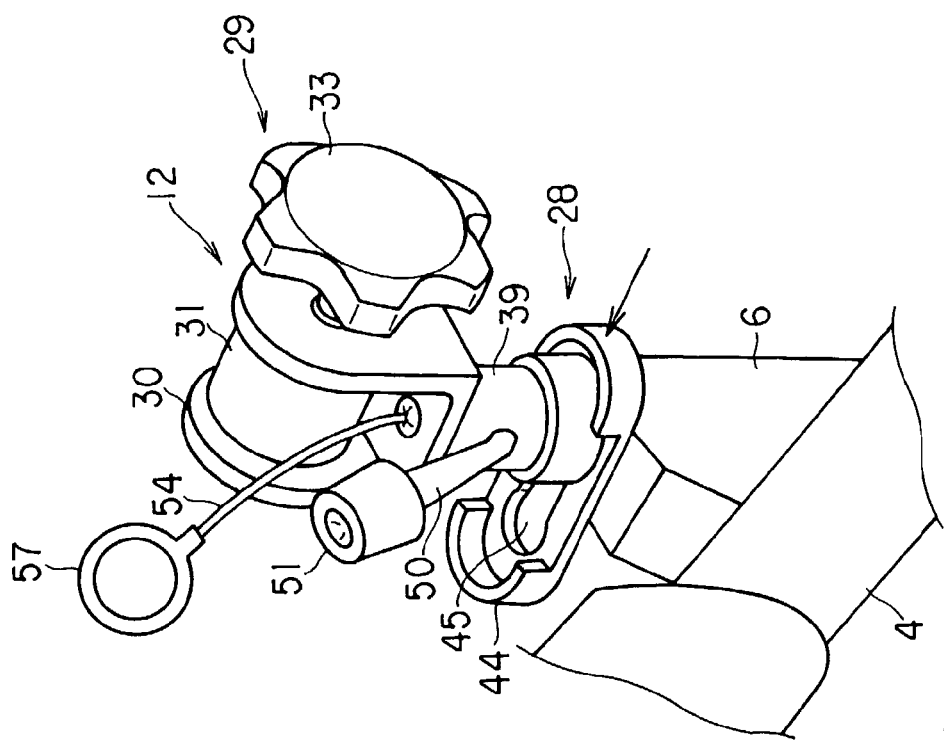
FIG. 10A is a perspective view of primary parts showing the state before coupling the operation portion of the endoscopic ligation apparatus according to the first embodiment and the mouth ring portion of the operation portion of the endoscope.

In addition, substantially straight guide grooves 48 and 49 are formed on the both sides of a part at which the large-diameter hole portion 45, the communication portion 47 and the engagement hole portion 46 of the sliding member 44 are formed. The sliding guides 41 and 42 of the shaft portion 39 are inserted to the guide grooves 48 and 49, respectively. Additionally, with the guide grooves 48 and 49 being sliding along the sliding guides 41 and 42 of the shaft portion 39, the large-diameter hole portion 45 of the sliding member 44 is supported so as to be capable of sliding between a first position at which the large-diameter hole portion 45 is arranged to be opposed to the fitting hole portion 40 of the shaft portion 39 as shown in FIG. 10A and a second position at which the engagement hole portion 46 is arranged so as to be opposed to the fitting hole portion 40 of the shaft portion 39.

Further, a base end portion of a substantially tubular water supply mouth ring 50 is fixed to the shaft portion 39 of the attachment portion 28. A lumen 50a of the water supply mouth ring 50 is caused to communicate with the fitting hole portion 40 of the shaft portion 39.

Furthermore, a syringe packing 51 is attached at the end portion of the water supply mouth ring 50. A syringe insertion valve 52 is provided to the syringe packing 51. The valve 52 of the syringe packing 51 is constituted by a straight slit formed to, e.g., a rubber sheet. Moreover, in the normal condition that the syringe 53 is not inserted, the lumen 50a of the water supply mouth ring 50 is closed, and a flow of air to the lumen 50a, the fitting hole portion 40, the through hole 10 and the forceps channel 5 is maintained to be intercepted. In addition, when the syringe 53 is inserted into the valve 52 of the syringe packing 51 of the water supply mouth ring 50, the valve 52 of the syringe packing 51 is elastically deformed and expands its diameter, and the sealing state of the syringe 53 at the insertion portion can be maintained by fixing the syringe 53 in the pressure welded state.

Figure 8:
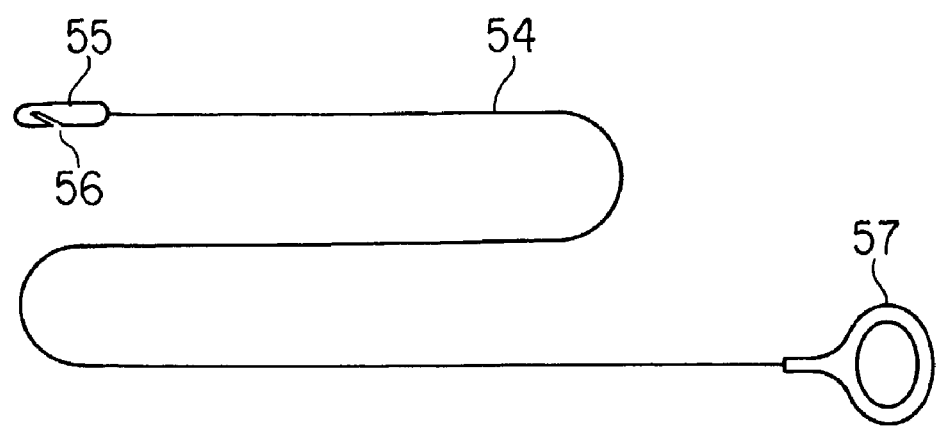
FIG. 8 is a plane view showing a pulling cord used in combination with the endoscopic ligation apparatus according to the first embodiment.

Additionally, a pulling cord 54 shown in FIG. 8 which is used when attaching the end attachment 11 to the end portion 3a of the insertion portion 3 of the endoscope 2 is provided to the endoscopic ligation apparatus 1 according to this embodiment separately from the end attachment 11, the operation cord 21 and the ligation band operation unit 12. The pulling cord 54 has a dimension that it can be inserted to the end portion 3a of the insertion portion 3 of the endoscope 2 from the ligation band operation unit 12 through the channel 5 of the endoscope 2.

Further, a hook member 55 is provided at the end portion of the pulling cord 54. To the hook member 55 is formed a notch 56 with which the operation cord 21 can be engaged. Furthermore, an operation ring 57 is fixed at the front side end portion of the pulling cord 54.

Subsequently, the effect of the above-described structure will now be explained. When using the endoscopic ligation apparatus 1 according to this embodiment, there are sequentially carried out the operation (first operation) for detachably coupling the ligation band operation unit 12 to the mouth ring portion 6 of the operation portion 4 of the endoscope 2, the operation (second operation) for attaching the end attachment 11 to the end portion 3a of the insertion portion 3 of the endoscope 2, the operation (third operation) for attaching the operation cord 21 to the ligation band operation unit 12, and the operation (fourth operation) for ligating the living tissues as follows.

(1) Attachment of Ligation Band Operation Unit 12 to Endoscope 2 (First Operation)

The pulling cord 54 is inserted into the ligation band operation unit 12 in advance. At this moment, the pulling cord 54 is previously inserted through the fitting hole portion 40 of the attachment portion 28. Thereafter, the pulling cord 54 is inserted to the end portion 3a of the insertion portion 3 of the endoscope 2 through the forceps channel 5 of the endoscope 2. Further, as shown in FIG. 11A, the hook member 55 at the end of the pulling cord 54 is caused to protrude from the end portion 3a of the endoscope 2.

Then, the ligation band operation unit 12 is attached to the mouth ring portion 6 of the operation portion 4 of the endoscope 2. At this moment, at the attachment portion 28 of the ligation band operation unit 12, the large-diameter hole portion 45 of the sliding member 44 is set coaxial by arranging the large-diameter hole portion 45 so as to be opposed to the fitting hole portion 40 of the shaft portion 39. In this state, as shown in FIG. 10A, the large-diameter hole portion 45 of the sliding member 44 and the fitting hole portion 40 of the shaft portion 39 are fitted to the mouth ring portion 6 of the endoscope 2, and the seat 7 is brought into contact with the shaft portion 39.

Figure 10B:
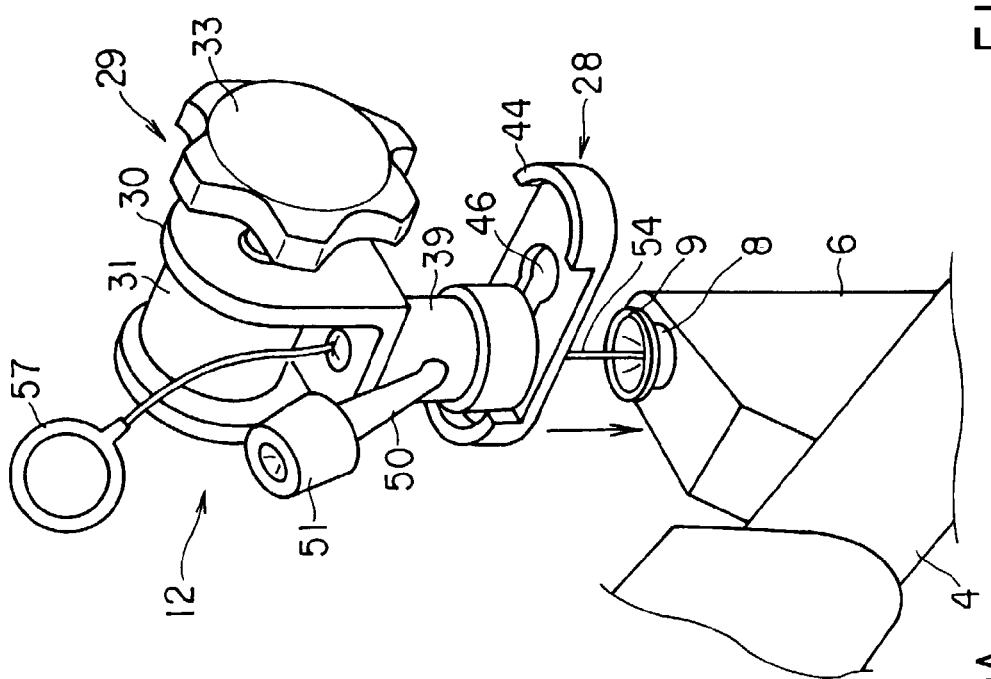
FIG. 10B is a perspective view of primary parts showing the coupling state between the operation portion of the endoscopic ligation apparatus and the mouth ring portion of the operation portion.

Subsequently, the sliding member 44 is operated to slide in the guiding direction of the sliding guides 41 and 42 and the guide grooves 48 and 49 of the sliding member 44. Then, as shown in FIG. 10B, the engagement hole portion 46 of the sliding member 44 is positioned coaxially with the fitting hole portion 40. At this moment, as shown in FIG. 9, with the flange portion 9 of the mouth ring portion 6 being inserted in the fitting hole portion 40 of the shaft portion 39, the engagement hole portion 46 of the sliding member 44 is engaged being pressed into the protrusion portion 8 of the mouth ring portion 6. As a result, the attachment portion 28 of the ligation band operation unit 12 is fixed to the mouth ring portion 6 of the operation portion 4 of the endoscope 2.

Furthermore, in the state that the engagement hole portion 46 of the sliding member 44 is engaged with the protrusion portion 8 of the mouth ring portion 6 in this manner, the flange portion 9 is held being welded to the packing 43 in the fitting hole portion 40 with pressure. At this moment, since the packing 43 receives the pressing force from the flange portion 9 side and presses the shaft portion 39, a flow of air to the forceps channel 5 from the outside through the fitting hole portion 40 and the through hole 10 can be intercepted.

(2) Attachment of End Attachment 11 to Endoscope 2 (Second Operation)

When performing this operation, the base end portion side of the operation cord 21 is engaged with the notch 56 of the hook member 55 of the pulling cord 54 caused to protrude from the end portion 3a of the insertion portion 3 of the endoscope 2 to the outer side. At this moment, as shown in FIG. 11A, with the operation cord 21 being caught by the notch 56 of the hook member 55, any one of the fixation beads 27 at the base end portion of the operation cord 21 is engaged so as to be held.

Subsequently, the operation ring 57 of the pulling cord 54 is held, and the pulling cord 54 is pulled toward the front side. By this operation, the fixation bead 27 and the operation cord 21 are pulled from the end portion 3a of the insertion portion 3 in the endoscope 2 into the forceps channel 5 after the hook member 55. Then, when the pulling cord 54 is pulled out from the forceps channel 5 of the endoscope 2 to the outside through the ligation band operation unit 12, the fixation beads 27 engaged with the hook member 55 are sequentially pulled out from the ligation band operation unit 12 together with the operation cord 21. In this state, the operation cord 21 is unset from the hook member 55 outside the ligation band operation unit 12.

Thereafter, as shown in FIG. 11B, the hood 14 of the end attachment 11 is attached to the end portion 3a of the insertion portion 3 in the endoscope 2. At this moment, since the hood 14 is constituted by a soft member, the joint part between the end portion 3a of the insertion portion 3 in the endoscope 2 and the hood 14 is securely fixed by frictional engagement.

Furthermore, as shown in FIG. 2B, fixation at a constant position is always enabled by thrusting the end portion 3a of the insertion portion 3 in the endoscope 2 until it comes into contact with the impingement portion 15 of the end attachment 11.

(3) Attachment of Operation Cord 21 to Ligation Band Operation Unit 12 (Third Operation)

When performing this operation, as shown in FIG. 11C, the operation cord 21 pulled from the ligation band operation unit 12 is first pulled toward the front side, and the slack of the operation cord 21 in the forceps channel 5 of the endoscope 2 is taken up.

Subsequently, the operation cord 21 is inserted to the opening end side of the operation cord attachment groove 37 on the take-up drum 31 and engaged so as to be held by any of the fixation beads 27. Moreover, as shown in FIG. 11D, the operation cord 21 is pulled to the central axial side of the take-up drum 31 and one side of the fixation beads 27 on the front side engaged with the attachment groove 37 is engaged with the recess 38.

With the above-described operation, the operation cord 21 is fixed to the take-up drum 31 without the slack in accordance with the length of the forceps channel 5 of the endoscope 2.

(4) Ligation of Living tissue (Fourth Operation)

When performing this operation, the insertion portion 3 of the endoscope 2 to which the endoscopic ligation apparatus 1 according to this embodiment is first inserted into the body of a patient. Then, the end attachment 11 is brought into contact with a target living tissue while observing an image of the inside of the body by using the endoscope 2.

Subsequently, the suction force is applied through the forceps channel 5 of the endoscope 2, and the living tissue is drawn into the end attachment 11. In this state, the handle 33 of the ligation band operation unit 12 is rotated. Here, the handle 33 starts to rotate from the step 90a of one engagement cam 34a of the take-up drum 31, and rotation of the handle 33 is continued until the claw 35 engages with the next step 90b of the engagement cam 34b.

At this moment, since the interval L1 between the respective operation beads 22 to 26 is set to a half of the circumferential length of the take-up drum 31, namely, the length corresponding to the interval between the two engagement cams 34a and 34b, only the operation bead 22 set at the position closest to the end portion side moves on the tubular member 13 toward the end portion side even in one stroke for rotating the handle 33 from the engagement position with one engagement cam 34a to the engagement position with the other engagement cam 34b. Then, the ligation band 16 placed at the position closest to the end side comes off the end portion side of the tubular member 13 with the movement of the operation bead 22.

Since the claw 35 is made up of a material having the resiliency, it hits the surface of the take-up drum 31 with the force of repulsion at the moment that the claw 35 engages with the step 90b. At this time, since a cavity 91 is formed in the take-up drum 31, the echo occurs in the cavity 91 and the loud sound is generated. Therefore, an operator can recognize the end of one ligation operation by the hand feeling and the sound when the step 90b engages with the claw 35 even if he/she does not confirm the screen of the endoscope.

The ligation band 16 which has come off the tubular member 13 and to which the living tissue is fitted contracts to the diameter in the natural state, and ligates the tissue of the living body by its contraction force.

By repeating the above-described operations and manipulating the five operation beads 22 to 26 in order, the five ligation bands 16 to 20 sequentially come off the end portion of the tubular member 13, and a plurality of living tissue are continuously ligated by the respective ligation bands 16 to 20. Then, when the operation for ligating a necessary number of living tissue is finished, the insertion portion 3 of the endoscope 2 is removed from the body of a patient, thereby terminating the treatment.

Thus, the apparatus having the above-described structure demonstrates the following advantages. That is, in this embodiment, in the operation for coupling the ligation band operation unit 12 to the mouth ring portion 6 of the operation portion 4 in the endoscope 2, the flange portion 9 of the mouth ring portion 40 is engaged with the engagement hole portion 46 of the sliding member 44 being pressed into the protrusion portion 8 of the mouth ring portion 6 by the operation of the sliding member 44 of the ligation band operation unit 12. Therefore, attachment of the ligation band operation unit 12 coupled to the mouth ring portion 6 of the operation portion 4 in the endoscope 2 does not become loose even in the ligation operation. Accordingly, since secure fixation is enabled as compared with fixation by frictional engagement, the slack or movement does not occur even if large force is applied to the attachment portion of the ligation band operation unit 12 during the treatment, thereby performing the treatment with the excellent operational feeling.

Moreover, since the ligation band operation unit 12 can be attached or detached by only the simple sliding operation of the sliding member 44, the operability of the attachment/detachment operation of the ligation band operation unit 12 can be improved.

In addition, since each of a plurality of the operation beads 22 to 26 at the end portion of the operation cord 21 is formed into a shape that the length of each bead in the axial direction of the operation cord 21 is larger than the outside diameter, the following advantages can be expected.

That is, a large surface area of each of the operation beads 22 to 26 when attached to the end attachment 11 can be assured while maintaining the function for driving the ligation bands 16 to 20 of the operation beads 22 to 26.

Additionally, since the operation beads 22 to 26 are aligned in a line in the axial direction when the operation cord 21 is wound around the outer periphery of the tubular member 13, all the operation beads 22 to 26 can have the smooth shape with respect to the tubular member 13, the endoscope 2 can be smoothly inserted into a patient without the resistance.

Further, since a plurality of the fixation beads 27 are formed at the front end portion of the operation cord 21, the operation cord 21 can be always adjusted to have no slack and attached even if the entire length of the forceps channel 5 varies depending on types of the endoscopes 2. Therefore, the click operation generated by the engagement cam 24a and 24b and the claw 35 in the ligation band operation unit 12 can be matched with the ligation operation of the ligation bands 16 to 20 irrespective of types of the endoscope 2, thereby improving the operational feeling.

Furthermore, in the endoscopic ligation apparatus 1 which is the endoscopic instrument according to this embodiment, the endoscopic ligation apparatus 1 can be assembled to the endoscope 2 by the simple operation, and the treatment time can be advantageously shortened.

Figure 12:
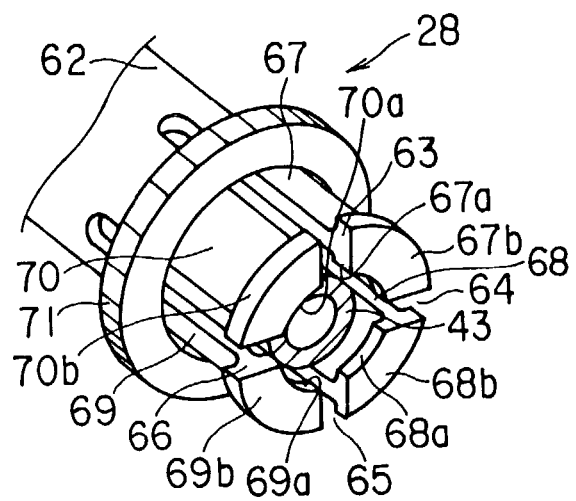
FIG. 12 is a perspective view of primary parts showing and endoscopic ligation apparatus according to a second embodiment of the present invention.
Figure 13A:
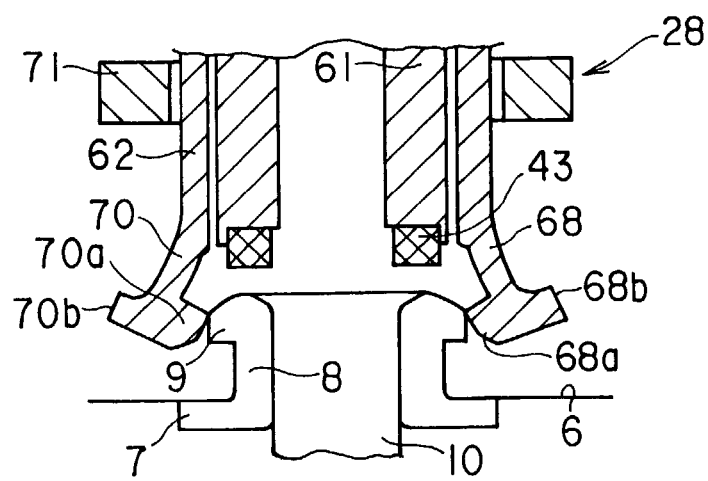
FIG. 13A is a vertical cross-sectional view of primary parts showing the state in which a restriction stopper of the endoscopic ligation apparatus according to the second embodiment is positioned on the front side of an attachment portion.
Figure 13B:
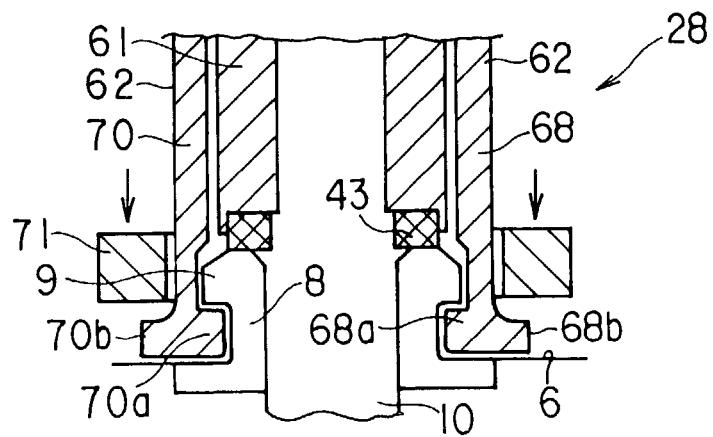
FIG. 13B is a vertical cross-sectional view of primary parts showing the state in which the restriction stopper is moved to the mouth ring side and the attachment portion is fixed to the mouth ring.

Moreover, FIGS. 12 to 13B show a second embodiment according to the present invention. In this embodiment, the structure of the ligation band operation unit 12 of the endoscopic ligation apparatus 1 according to the first embodiment (see FIGS. 1 to 11) is changed as follows. Incidentally, in FIGS. 12 to 13B, like reference numerals denote like or corresponding parts equal to those of the endoscopic ligation apparatus 1 according to the first embodiment, and their explanation is omitted here.

That is, in this embodiment, as shown in FIGS. 13A and 13B, a substantially cylindrical outer cylindrical member 62 is provided to the outside of the substantially cylindrical shaft portion 61 in the attachment portion 28 of the ligation band operation unit 12.

In addition, four slits 63 to 66 are axially extended to the outer cylindrical member 62 on the joint end portion side between the member 62 and the mouth ring portion 6 of the endoscope 2. These slits 63 to 66 are arranged at equal intervals and formed into a substantially X shape. Additionally, four leg portions 67 to 70 having an appropriate length are formed by the parts between the respective slits 63 to 66 of the outer cylindrical member 62.

Further, inner claws 67a to 70a and outer claws 67b to 70b are provided at the end portions of the respective leg portions 67 to 70 so as to protrude toward the inside and outside. Here, the inside diameter dimension of the inner peripheral surface of each of the leg portions 67 to 70 is set to be substantially equal to the outside diameter dimension of the flange portion 9 of the mouth ring portion 6. Furthermore, the inside diameter of the inner claws 67a to 70a of respective leg portions 67 to 70 is set to be substantially equal to the diameter of the protrusion portion 8.

Moreover, an operation ring 71 which moves along the outer cylindrical member 62 in the axial direction is provided to the outer peripheral surface of the outer cylindrical member 62. The inside diameter dimension of the operation ring 71 is set smaller than the outside diameter dimension of the outer claws 67b to 70b of the respective leg portions 67 to 70. In addition, when the attachment portion 28 of the ligation band operation unit 12 is attached to the mouth ring portion 6 of the endoscope 2, the operation ring 71 switches between an engagement position at which these members are held in the engagement state and an engagement releasing position at which engagement between these members is released.

The effect of this embodiment having the above-described structure will now be described. In this embodiment, in the operation for attaching the attachment portion 28 of the ligation band operation unit 12 to the mouth ring portion 6 of the operation portion 4, the operation ring 71 is arranged at the position above the outer cylindrical member 62 in advance as shown in FIG. 13A.

In this state, the attachment portion 28 of the ligation band operation unit 12 is fitted on the mouth ring portion 6 of the endoscope 2. At this moment, although the inside diameter dimension of the inner claws 67a to 70a of the respective leg portions 67 to 70 of the outer cylindrical member 62 is smaller than the outside diameter dimension of the flange portion 9, the respective leg portions 67 to 70 of the outer cylindrical member 62 can be elastically deformed toward the outer direction by the slits 63 to 66. Therefore, the respective inner claws 67a to 70a get over the flange portion 9 as shown in FIG. 13A and engage with the protrusion portion 8 as shown in FIG. 13B.

Subsequently, as shown in FIG. 13B, the operation ring 71 is moved to the mouth ring portion 6 side of the endoscope 2 as shown in FIG. 13B. At this moment, by moving the operation ring 71 to a position at which it is brought into contact with the outer claws 67b to 70b of the respective leg portions 67 to 70, the operation ring 71 is positioned on substantially the same plane as the protrusion portion 8. In this state, the inner claws 67a to 70a of the respective leg portions 67 to 70 engage with the protrusion portion 8, and elastic deformation of the outer cylindrical member 62 in the outer direction due to the slits 63 to 66 is restricted by the operation ring 71. Therefore, the attachment portion 28 of the ligation band operation unit 12 is fixed to the mouth ring portion 6 of the operation portion 4 of the endoscope 2.

Thus, in the operation for coupling the ligation band operation unit 12 to the mouth ring portion 6 of the operation portion 4 in the endoscope 2, it is possible to perform the operation for switching between the engagement position at which the attachment portion 28 of the ligation operation unit 12 and the mouth ring portion 6 of the endoscope 2 are held in the engagement state when the attachment portion 28 is attached to the mouth ring portion 6 and the engagement releasing position for releasing engagement between these members by the operation for moving the operation ring 71 of the ligation band operation unit 12 along the outer cylindrical member 62 in the axial direction. Therefore, this embodiment can obtain the advantage similar to that of the first embodiment.

Figure 14:
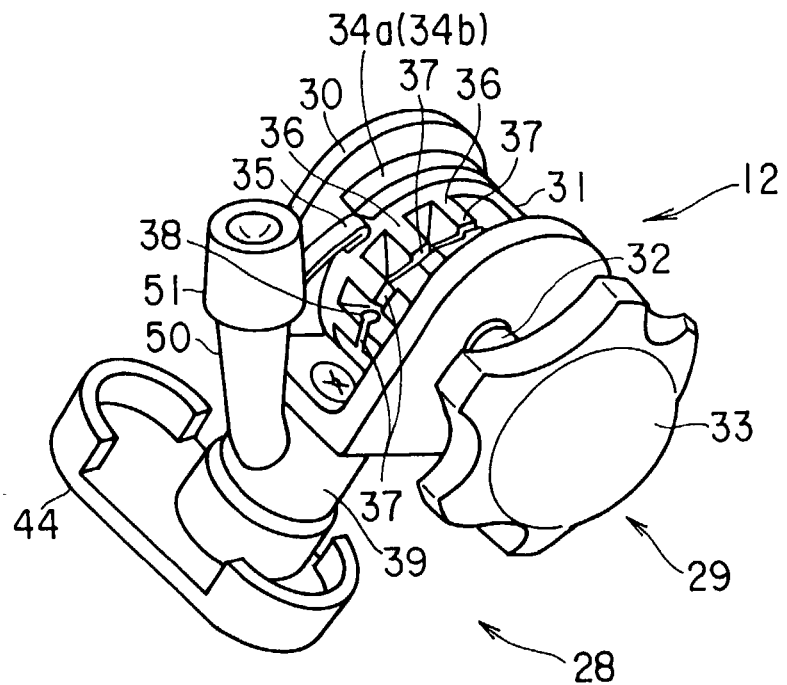
FIG. 14 is a perspective view showing an exterior appearance of an operation portion of an endoscopic ligation apparatus according to a third embodiment of the present invention.
Figure 15:
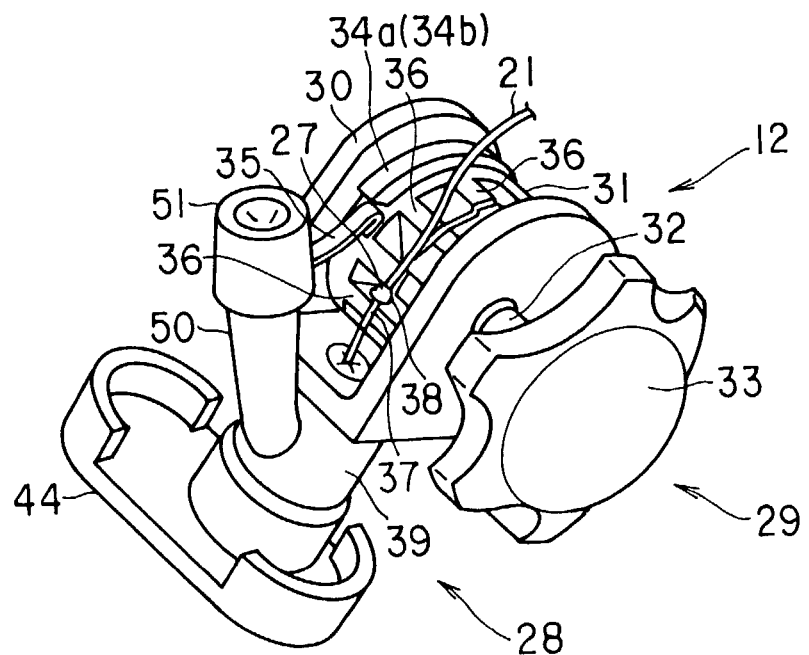
FIG. 15 is a perspective view of primary parts illustrating the effect of the operation portion of the endoscopic ligation apparatus according to the third embodiment.

Further, FIGS. 14 and 15 show a third embodiment according to the present invention. In this embodiment, the structure of the ligation band operation unit 12 in the endoscopic ligation apparatus 1 according to the first embodiment (see FIGS. 1 to 11D) is changed as follows. Incidentally, in FIGS. 14 and 15, like reference numerals denote parts equal to those in the endoscopic ligation apparatus 1 according to the first embodiment, and their explanation is omitted here.

That is, in this embodiment, only one fixation bead 27 is provided to the front side end portion of the operation cord 21, a plurality of cord fixation portions 36 are provide on the outer peripheral surface of the take-up drum 31 in the ligation band operation unit 12, and an operation cord attachment groove 37 and a recess 38 with which the fixation beads 27 of the operation cord 21 can engage are provided to each cord fixation portion 36.

The effect of the above-described structure will now be described. In this embodiment, in the operation for attaching the operation cord 21 to the ligation band operation unit 12, the operation cord 21 drawn from the ligation band operation unit 12 is pulled to the front side, and the slack of the operation cord 21 in the forceps channel 5 is taken up.

Subsequently, as shown in FIG. 15, the operation cord 21 is inserted to the operation cord attachment groove 37 of the cord fixation portion 36 at any position on the take-up drum 31, and the fixation bead 27 is engaged. Further, the operation cord 21 is led to the central axial side of the take-up drum 31, and the fixation bead 27 is engaged with the recess 38 at any position.

With the above-described operation, the operation cord 21 is fixed to the take-up drum 31 without the slack in accordance with the length of the forceps channel 5 of the endoscope 2.

Thus, in this embodiment, the endoscopic ligation apparatus 1 can be used as similar to the first embodiment, thereby obtaining the same advantage as that in the first embodiment.

Figure 16A:
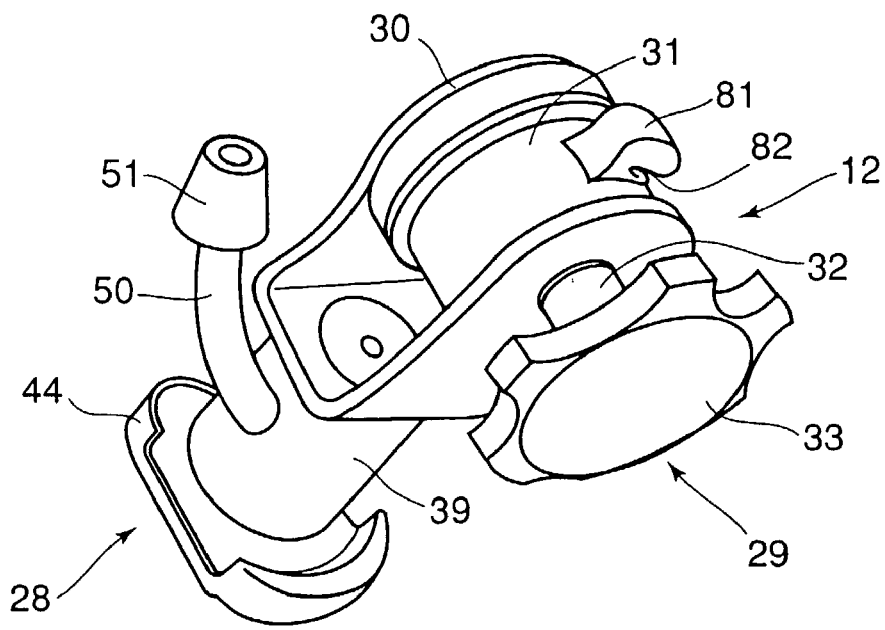
FIG. 16A is a perspective view showing an exterior appearance of an operation portion of an endoscopic ligation apparatus according to a fourth embodiment of the present invention.
Figure 16B:
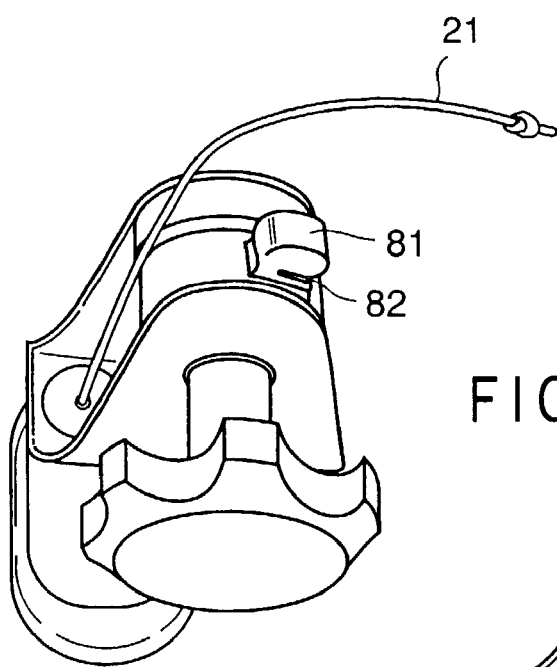
FIG. 16B is a perspective view of primary parts of the operation portion showing the state in which the operation cord is held in a slit on the take-up drum and engaged by friction.
Figure 16C:
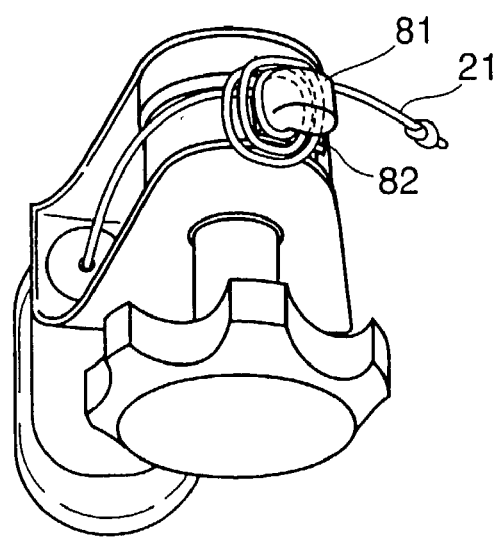
FIG. 16C is a perspective view of primary parts of the operation portion showing the state in which the operation cords is wound around an engagement hook by two or three turns and engaged therewith.
Figure 17:
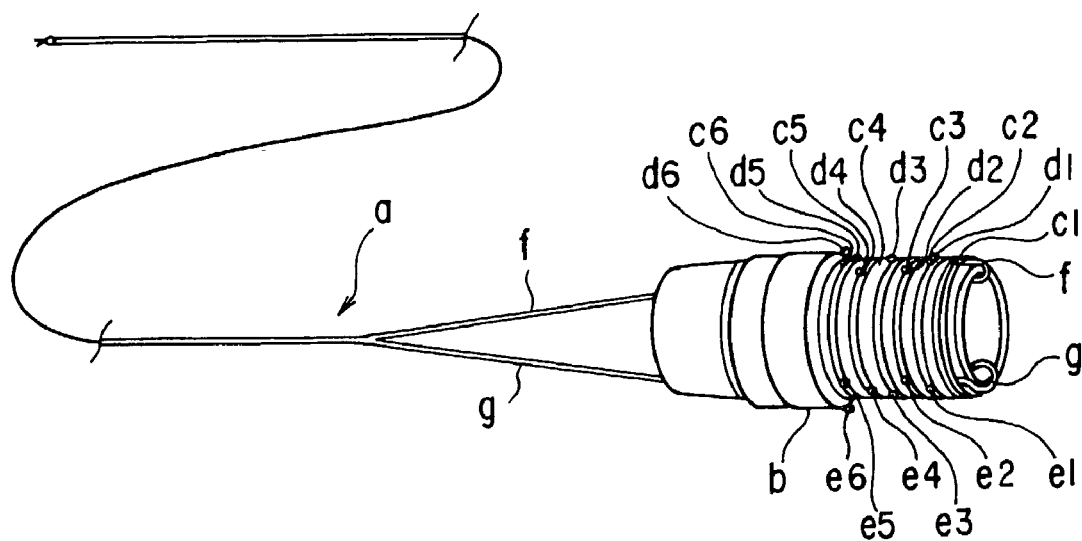
FIG. 17 is a perspective view showing a schematic structure of a prior art ligator.
Figure 18A:
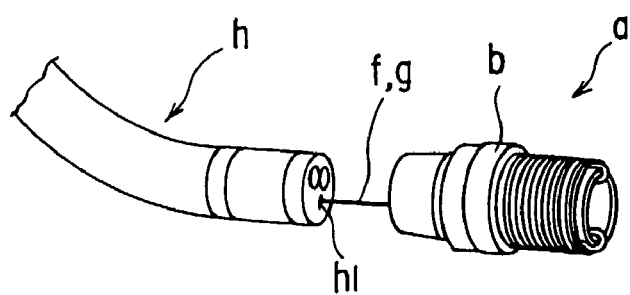
FIG. 18A is a perspective view of primary parts showing the state before attaching a tubular member of the prior art ligator to an end of an insertion portion of an endoscope.
Figure 18B:
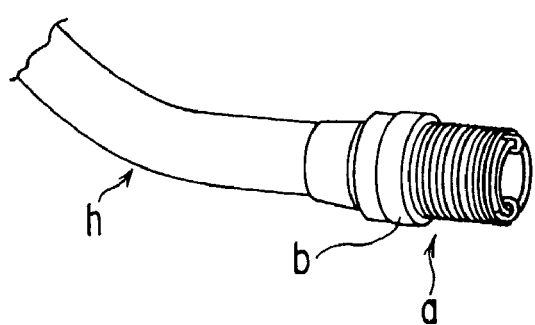
FIG. 18B is a perspective view of primary parts showing the state in which the tubular member of the prior art ligator is attached to the end of the insertion portion of the endoscope.
Figure 19A:
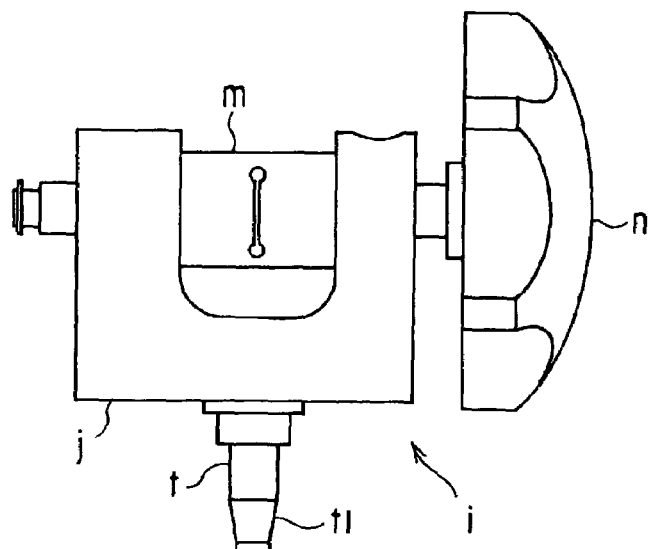
FIG. 19A is a perspective view showing a structural example of the operation portion for pulling the operation cord toward the front side.
Figure 19B:
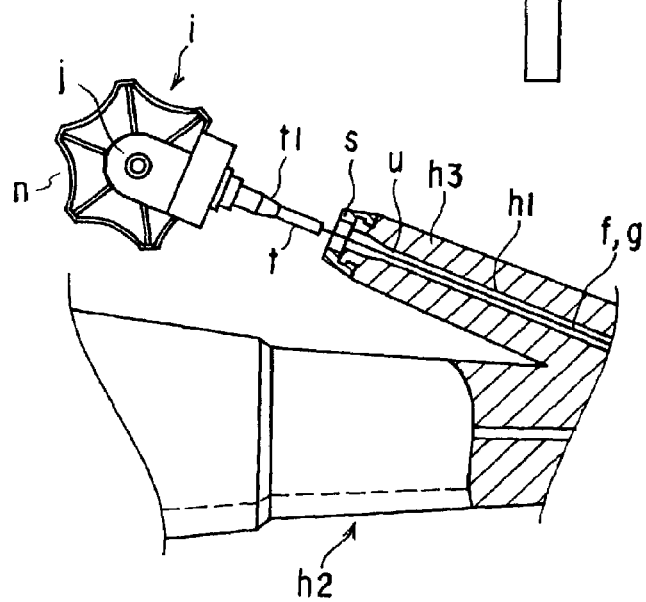
FIG. 19B is a partially cross-sectional side view showing the state before inserting the take-up shaft of the operation portion into the mouth ring portion of the operation portion of the endoscope.
Figure 19C:
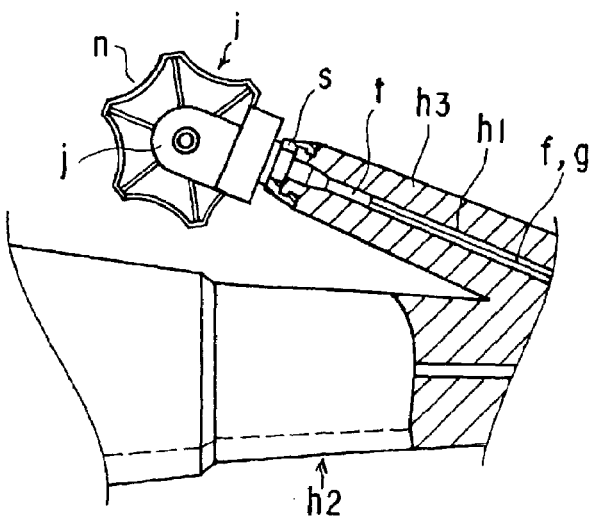
FIG. 19C is a partially cross-sectional side view showing the state in which the take-up shaft of the operation portion is inserted into the mouth ring of the operation portion of the endoscope.
Figure 20:
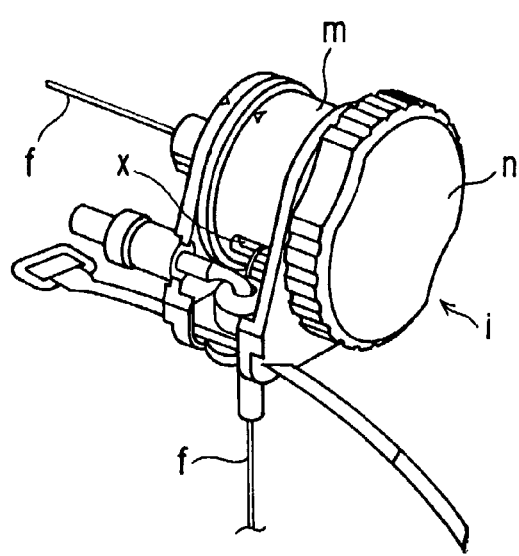
FIG. 20 is a perspective view showing another prior art of the operation portion which applies the tension to the operation cord.
Figure 21:
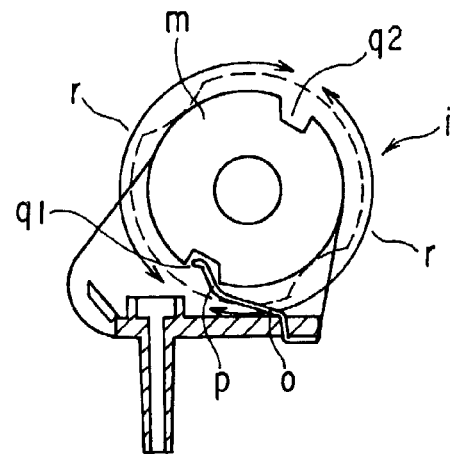
FIG. 21 is a vertical cross-sectional view of primary parts showing the structure of the periphery of the take-up shaft in the operation portion.
Figure 22:
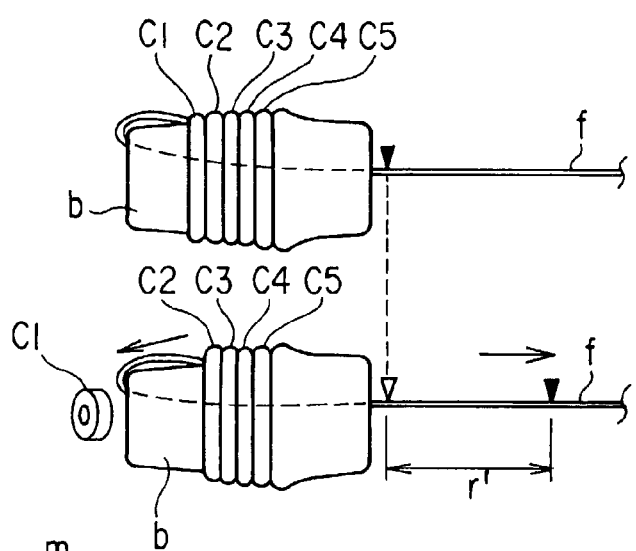
FIG. 22 is an explanatory view illustrating the operation for removing an elastic ligation ring from the tubular member of the ligator.
Figure 23:
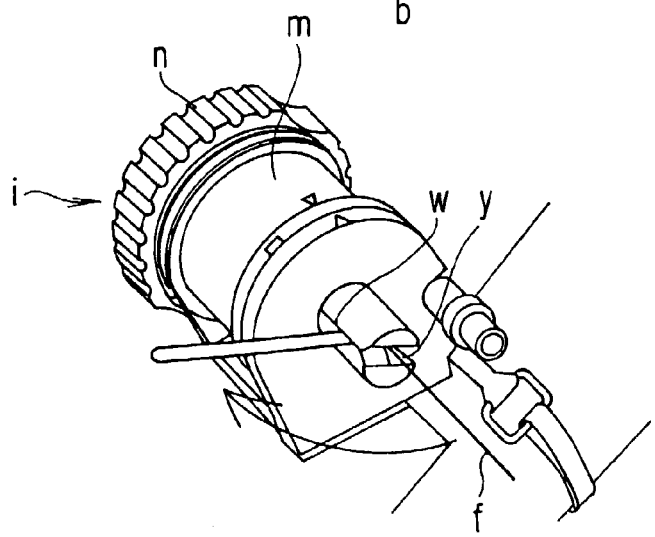
FIG. 23 is a perspective view of primary parts showing the state in which the operation cord is fixed to the slit of the take-up shaft.

Furthermore, FIGS. 16A to 16C show a fourth embodiment according to the present invention. In this embodiment, the structure of the ligation band operation unit 12 of the endoscopic ligation apparatus 1 according to the first embodiment (see FIGS. 1 to 11D) is changed as follows. Incidentally, in FIGS. 16A to 16C, like reference numerals denote parts equal to those in the endoscopic ligation apparatus 1 according to the first embodiment, and their explanation is omitted here.

That is, in this embodiment, as shown in FIG. 16A, one engagement hook 81 is provided so as to protrude on the outer peripheral surface of the take-up drum 31 in the ligation band operation unit 12, and engagement members such as the fixation beads 27 on the operation cord 21 are eliminated. Furthermore, a cord attachment slit 82 is formed to the engagement hook 81.

The effect of the above-described structure will now be described. In this embodiment, in the operation for attaching the operation cord 21 to the ligation band operation unit 12, the operation cord 21 drawn out from the ligation band operation unit 12 is pulled toward the front side and the slack of the operation cord 21 in the forceps channel 5 is taken up as shown in FIG. 16B.

Subsequently, the operation cord 21 is held in the slit 82 of the engagement hook 81 on the take-up drum 31 and engaged by friction. Moreover, as shown in FIG. 16C, the operation cord 21 is wound around the engagement hook 81 by two or three turns.

With the above-described operation, the operation cord 21 is fixed to the take-up drum 31 without the slack in accordance with the length of the forceps channel 5.

Thus, the endoscopic ligation apparatus 1 can be used in this embodiment having the above-described structure as similar to the first embodiment, thereby obtaining the advantages similar to those in the first embodiment. Further, in this embodiment in particular, since one engagement hook 81 is provided so as to protrude on the outer peripheral surface of the take-up drum 31, the operation cord 21 and the take-up drum 31 can be assuredly fixed by winding the operation cord 21 around the engagement hook 81. Accordingly, since any engagement member does not have to be provided on the operation cord 21, there can be obtained an advantage of reducing a number of components/machining points and a cost price of a product in addition to the advantages of the first embodiment.

In addition, the present invention is not restricted to the foregoing embodiments and can be, of course, modified in many ways without departing from the scope of the present invention.

What is claimed is:

1. An endoscopic instrument,
an operation portion of an endoscope having a mouth ring of a channel which is inserted through a main body of said endoscopic instrument used in combination with said endoscope,
said mouth ring portion having a protrusion portion which protrudes from said operation portion toward the outer side and a flange portion arranged at an edge portion of said protrusion portion,
said endoscopic instrument main body having an attachment portion attached to said mouth ring,
wherein said attachment portion has a mouth ring fitting portion fitted to said mouth ring portion,
said mouth ring fitting portion having:
a cylindrical shaft portion including at a shaft center portion a fitting hole portion fitted to said mouth ring portion; and
an engagement operation portion which is supported on said shaft portion and operates to switch between a flange portion insertion position at which said flange portion of said mouth ring portion can be inserted and an engagement position at which it can be engaged with said protrusion portion of said mouth ring.

2. The endoscopic instrument according to claim 1, wherein said engagement operation portion has a sliding member capable of moving along said protrusion portion, said sliding member having a guide hole into which said protrusion portion of said mouth ring is slidably inserted; and
wherein said guide hole has a large-diameter portion into which said flange portion of said mouth ring portion can be inserted, an engagement hole portion with which said protrusion portion of said mouth ring can be engaged, and a communication portion which communicates between said large-diameter hole portion and said engagement hole portion.

3. The endoscopic instrument according to claim 2, wherein said engagement operation portion has an actuation guide which guides the sliding operation that said sliding member moves along said guide hole between an engagement releasing position at which said protrusion portion is inserted to said large-diameter hole portion and an engagement position at which said protrusion portion is engaged with said engagement hole portion.

4. The endoscopic instrument according to claim 3, wherein said actuation guide has a guide groove formed to said sliding member in contiguity with at least one side portion part of said guide hole; and
wherein said shaft portion has a sliding guide inserted to said guide groove.

5. The endoscopic instrument according to claim 1, wherein said endoscopic instrument main body is an endoscopic ligation apparatus which ligates a living tissue.

6. The endoscopic instrument according to claim 5, wherein said endoscopic ligation apparatus comprises:
a substantially cylindrical attachment which can be attached at an end part of an insertion portion of said endoscope and has a ligation band which ligates a living tissue being detachably fitted thereon;
an operation cord inserted into said channel, said operation cord having an end portion at which an engagement portion detachably engaging with said ligation band is arranged and a base end portion which extends to said operation portion side; and
a ligation band operation portion which is attached to said mouth ring and gives tensile force toward the front side to said operation cord.

7. The endoscopic instrument according to claim 6, wherein said attachment has a plurality of said ligation bands;
wherein said operation cord has a plurality of anchor members which respectively engage with said respective ligation bands; and
wherein said anchor member is formed into a cylindrical shape coaxial with said operation cord.

8. The endoscopic instrument according to claim 7, wherein said anchor member is set in such a manner that a ratio of its length L2 in the axial direction of said operation cord and its length D1 in the radial direction is larger than 1.

9. The endoscopic instrument according to claim 6, wherein said operation cord has a plurality of said anchor members arranged at fixed intervals;
wherein said interval has substantially the same length as an outer peripheral length of said attachment; and
wherein said attachment has an anchor member alignment portion by which said anchor members are aligned in the axial direction of said attachment when said operation cord is spirally wound on the outer periphery of said attachment.

10. An endoscopic instrument used in combination with an endoscope, wherein said endoscopic instrument is an endoscopic ligation apparatus which ligates a living tissue, said endoscopic ligation apparatus comprising:
an attachment which can be attached at an end of said endoscope and has at least one ligation band fitted thereon;
one operation cord which is inserted into a channel of said endoscope from said attachment;
an equipment operation portion which is fixed in the vicinity of said operation portion of said endoscope and gives a pulling operation toward the front side to said operation cord;
a take-up shaft of said operation cord which is supported by said equipment operation portion so as to be capable of swiveling;
a fixing portion of said operation cord which is provided on the peripheral surface of said take-up shaft; and a plurality of coupling points in a range where said operation cord and said equipment operation portion exist.

11. The endoscopic instrument according to claim 10, wherein said operation cord has a cord connection portion on the front side; and
wherein a plurality of either said fixing portions or said cord connection portions are provided at predetermined intervals.

12. The endoscopic instrument according to claim 11, wherein said endoscopic ligation apparatus has a plurality of said fixing portions and said one cord connection portion.

13. The endoscopic instrument according to claim 11, wherein said endoscopic ligation apparatus has said one fixing portion and a plurality of said cord connection portions.

14. An endoscopic instrument used in combination with an endoscope, wherein said endoscopic instrument is an endoscopic ligation apparatus which ligates a living tissue, said endoscopic ligation apparatus comprising:
an attachment which can be attached at an end of said endoscope and has at least one ligation band fitted thereon;
one operation cord which is inserted into a channel of said endoscope from said attachment;
an equipment operation portion which is fixed in the vicinity of an operation portion of said endoscope and gives a pulling operation toward the front side to said operation cord;
a take-up shaft of said operation cord, said take-up shaft having a cavity therein;
at least one engagement cam which restricts a rotational stroke of said take-up shaft; and
an engagement claw which engages with said engagement cam and has the elasticity which gives a rotational operation and a fixing operation of said take-up shaft.

15. An endoscopic instrument comprising:
a mouth ring fitting portion fittable to a mouth ring portion of an endoscope which comprises a protrusion portion and a flange portion provided at an edge portion of the protrusion portion;
a cylindrical shaft portion provided at the mouth ring fitting portion, and including a fitting hole portion fitted to the mouth ring portion; and
an engagement operation portion which is supported and movable in a direction substantially perpendicular to an axial direction of the shaft portion, and which operates to switch between a flange portion insertion position at which the flange portion of the mouth ring is inserted and an engagement position at which engagement of the protrusion portion of the mouth ring is achieved.

16. The endoscopic instrument according to claim 15, wherein said engagement operation portion has a sliding member capable of moving along said protrusion portion, said sliding member having a guide hole into which said protrusion portion of said mouth ring is slidably inserted; and
wherein said guide hole has a large-diameter portion into which said flange portion of said mouth ring portion can be inserted, an engagement hole portion with which said protrusion portion of said mouth ring can be engaged, and a communication portion which communicates between said large-diameter hole portion and said engagement hole portion.

17. The endoscopic instrument according to claim 16, wherein said engagement operation portion has an actuation guide which guides the sliding operation that said sliding member moves along said guide hole between an engagement releasing position at which said protrusion portion is inserted to said large-diameter hole portion and an engagement position at which said protrusion portion is engaged with said engagement hole portion.

18. The endoscopic instrument according to claim 17, wherein said actuation guide has a guide groove formed to said sliding member in contiguity with at least one side portion part of said guide hole; and
wherein said shaft portion has a sliding guide inserted to said guide groove.

19. The endoscopic instrument according to claim 15, wherein said endoscopic instrument main body is an endoscopic ligation apparatus which ligates a living tissue.

20. The endoscopic instrument according to claim 19, wherein said endoscopic ligation apparatus comprises:
a substantially cylindrical attachment which can be attached at an end part of an insertion portion of said endoscope and has a ligation band which ligates a living tissue being detachably fitted thereon;
an operation cord inserted into said channel, said operation cord having an end portion at which an engagement portion detachably engaging with said ligation band is arranged and a base end portion which extends to said operation portion side; and
a ligation band operation portion which is attached to said mouth ring and gives tensile force toward the front side to said operation cord.

21. The endoscopic instrument according to claim 20, wherein said attachment has a plurality of said ligation bands;
wherein said operation cord has a plurality of anchor members which respectively engage with said respective ligation bands; and
wherein said anchor member is formed into a cylindrical shape coaxial with said operation cord.

22. The endoscopic instrument according to claim 21, wherein said anchor member is set in such a manner that a ratio of its length $L2$ in the axial direction of said operation cord and its length $D1$ in the radial direction is larger than 1.

23. The endoscopic instrument according to claim 20, wherein said operation cord has a plurality of said anchor members arranged at fixed intervals;
wherein said interval has substantially the same length as an outer peripheral length of said attachment; and
wherein said attachment has an anchor member alignment portion by which said anchor members are aligned in the axial direction of said attachment when said operation cord is spirally wound on the outer periphery of said attachment.

* * * * *